US010213093B2

(12) United States Patent
Ichikawa et al.

(10) Patent No.: US 10,213,093 B2
(45) Date of Patent: Feb. 26, 2019

(54) FOCUS CONTROL DEVICE, ENDOSCOPE APPARATUS, AND METHOD FOR CONTROLLING FOCUS CONTROL DEVICE

(71) Applicant: OLYMPUS CORPORATION, Hachioji-shi, Tokyo (JP)

(72) Inventors: Manabu Ichikawa, Hachioji (JP); Toshiaki Mikami, Hachioji (JP); Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/613,085

(22) Filed: Jun. 2, 2017

(65) Prior Publication Data
US 2017/0265725 A1 Sep. 21, 2017

Related U.S. Application Data

(63) Continuation of application No. PCT/JP2014/081804, filed on Dec. 2, 2014.

(51) Int. Cl.
*H04N 5/225* (2006.01)
*H04N 5/232* (2006.01)
(Continued)

(52) U.S. Cl.
CPC ...... *A61B 1/00188* (2013.01); *A61B 1/00006* (2013.01); *A61B 1/00009* (2013.01);
(Continued)

(58) Field of Classification Search
CPC ............ A61B 1/00006; A61B 1/00009; A61B 1/00188; A61B 1/045; A61B 1/3132;
(Continued)

(56) References Cited

U.S. PATENT DOCUMENTS 5,416,515 A  5/1995  Arai et al.
9,219,854 B2 * 12/2015  Yoshino ............ H04N 5/23212
(Continued)

FOREIGN PATENT DOCUMENTS

JP   63017417 A   1/1988
JP   06189187 A   7/1994
(Continued)

OTHER PUBLICATIONS

International Search Report (ISR) and Written Opinion dated Mar. 3, 2015 issued in International Application No. PCT/JP2014/081804.

*Primary Examiner* — Marly S Camargo
(74) *Attorney, Agent, or Firm* — Holtz, Holtz & Volek PC

(57) ABSTRACT

A focus control device includes: a processor including hardware, the processor being configured to implement: an area setting process that sets a plurality of areas to a captured image that has been captured by an imaging section, each of the plurality of areas including a plurality of pixels; an object distance information calculation process that calculates distance information about a distance to an object that is captured within each of the plurality of areas; and a focus control process based on the distance information, wherein the processor implements the focus control process that performs a classification process that classifies the plurality of areas into a plurality of groups, and performs the focus control process based on area information about each of the plurality of groups.

20 Claims, 14 Drawing Sheets

(51) Int. Cl.
*H04N 5/369* (2011.01)
*A61B 1/00* (2006.01)
*A61B 1/31* (2006.01)
*A61B 1/04* (2006.01)
*G02B 7/34* (2006.01)
*A61B 1/045* (2006.01)
*A61B 1/313* (2006.01)
*G02B 23/24* (2006.01)
*G02B 23/26* (2006.01)

(52) U.S. Cl.
CPC ............ *A61B 1/045* (2013.01); *A61B 1/3132* (2013.01); *G02B 7/34* (2013.01); *H04N 5/2256* (2013.01); *H04N 5/23212* (2013.01); *H04N 5/23245* (2013.01); *H04N 5/3696* (2013.01); *G02B 23/2469* (2013.01); *G02B 23/26* (2013.01); *H04N 2005/2255* (2013.01)

(58) Field of Classification Search
CPC ............ H04N 5/2256; H04N 5/23212; H04N 5/23245; H04N 5/3696; G02B 7/34; G02B 23/26
USPC ..... 348/45, 65, 61, 345–350, 211.9; 396/17, 396/14, 79, 80, 82, 104, 121, 65; 600/163, 167, 101, 104, 117, 118, 145; 382/255, 133, 165, 170, 224, 227, 172, 382/270

See application file for complete search history.

(56) References Cited

U.S. PATENT DOCUMENTS

| | | | |
|---|---|---|---|
| 2011/0305446 A1* | 12/2011 | Itoh | G03B 13/34 396/95 |
| 2014/0039257 A1* | 2/2014 | Higuchi | G02B 7/34 600/109 |
| 2014/0210974 A1* | 7/2014 | Yoshino | H04N 5/23212 348/347 |
| 2016/0014328 A1* | 1/2016 | Rokutanda | G06T 7/0012 348/65 |

FOREIGN PATENT DOCUMENTS

| | | |
|---|---|---|
| JP | 06331883 A | 12/1994 |
| JP | 2002051255 A | 2/2002 |
| JP | 2006110055 A | 4/2006 |
| JP | 2006245792 A | 9/2006 |
| JP | 2011133559 A | 7/2011 |

* cited by examiner

FIG. 4

| G | R | G | R | G | R | G | R |
|---|---|---|---|---|---|---|---|
| B | G | B | G | B | G | B | G |
| G | S1 | G | S1 | G | S1 | G | S1 |
| B | G | B | G | B | G | B | G |
| G | S2 | G | S2 | G | S2 | G | S2 |
| B | G | B | G | B | G | B | G |
| G | R | G | R | G | R | G | R |
| B | G | B | G | B | G | B | G |

FIG. 14A (TISSUE MODE)
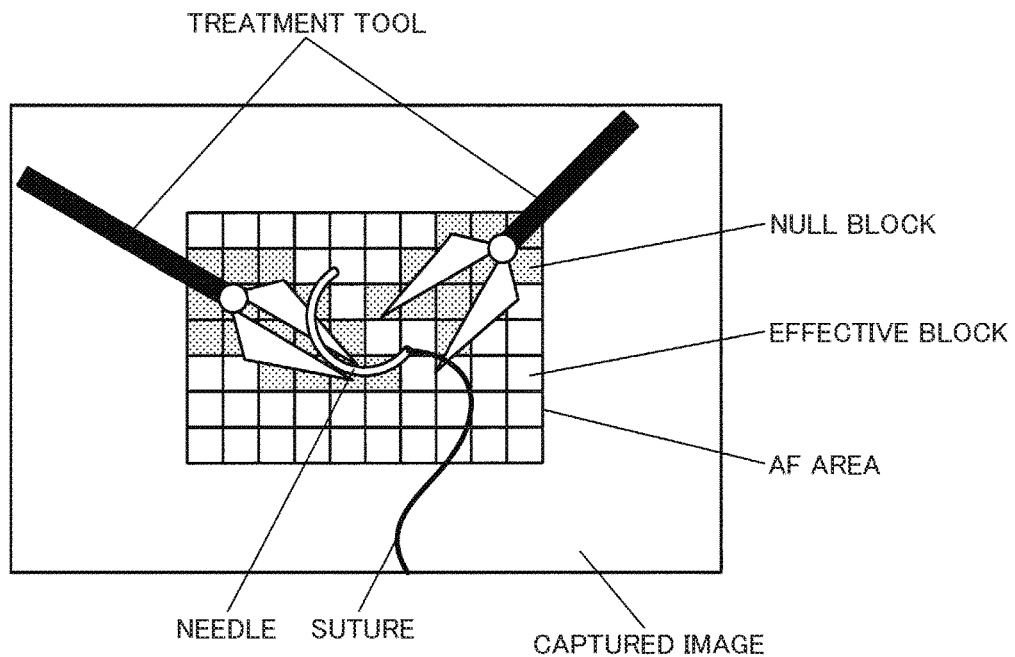
FIG. 14B (NEEDLE-SUTURE MODE)
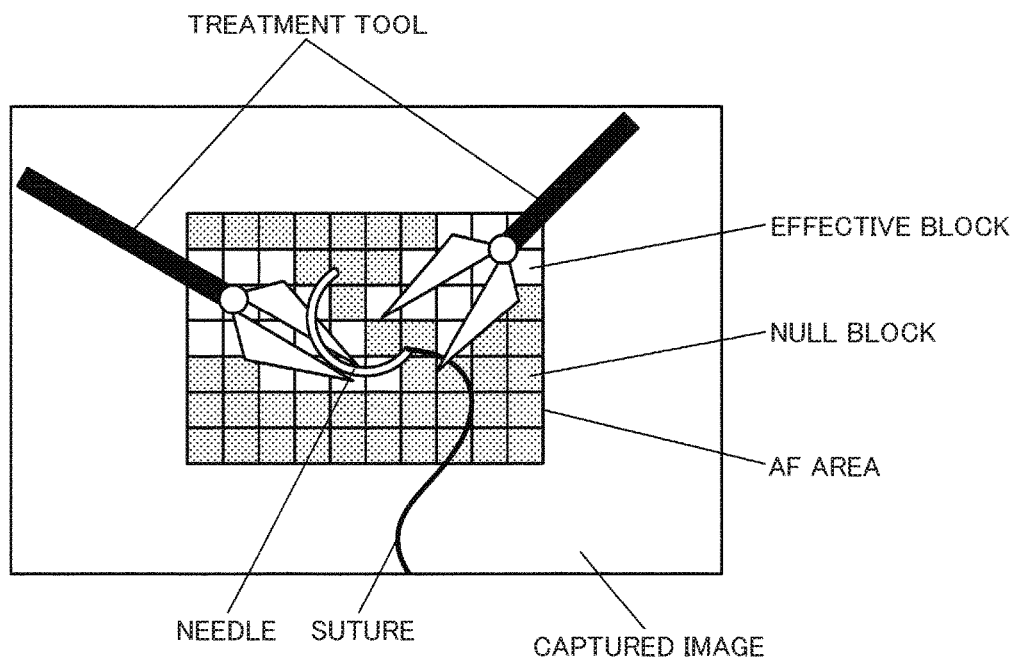

FOCUS CONTROL DEVICE, ENDOSCOPE APPARATUS, AND METHOD FOR CONTROLLING FOCUS CONTROL DEVICE

CROSS REFERENCE TO RELATED APPLICATION

This application is a continuation of International Patent Application No. PCT/JP2014/081804, having an international filing date of Dec. 2, 2014, which designated the United States, the entirety of which is incorporated herein by reference.

BACKGROUND

The present invention relates to a focus control device, an endoscope apparatus, a method for controlling a focus control device, and the like.

A depth of field as deep as possible is required for an endoscope system so that the user can easily perform diagnosis and treatment. In recent years, the depth of field of an endoscope system has become shallow along with the use of an image sensor having a large number of pixels, and an endoscope system that performs an autofocus (AF) process has been proposed.

A treatment (e.g., lesion excision and suture) may be performed during an endoscopic procedure, and a treatment tool (e.g., electrosurgical knife and forceps) may lie between tissue (that is brought into focus) and an endoscope system (imaging device). In such a case, the treatment tool that has a contrast higher than that of tissue may be brought into focus (i.e., tissue may not be brought into focus).

JP-A-2006-245792 discloses a method that prompts the user to designate an obstacle that lies between the object of interest and the imaging device so that the object of interest is brought into focus.

SUMMARY

According to one aspect of the invention, there is provided a focus control device comprising:

a processor comprising hardware, the processor being configured to implement:

an area setting process that sets a plurality of areas to a captured image that has been captured by an imaging section, each of the plurality of areas including a plurality of pixels;

an object distance information calculation process that calculates distance information about a distance to an object that is captured within each of the plurality of areas; and a focus control process based on the distance information, wherein the processor implements the focus control process that performs a classification process that classifies the plurality of areas into a plurality of groups based on the distance information, and brings a group among the plurality of groups into focus, the group that is brought into focus having an area which has been determined to be equal to or larger than a given threshold value based on area information about each of the plurality of groups.

According to another aspect of the invention, there is provided an endoscope apparatus comprising the above focus control device.

According to another aspect of the invention, there is provided a method for controlling a focus control device comprising:

setting a plurality of areas to a captured image that has been captured by an imaging section, each of the plurality of areas including a plurality of pixels;

calculating distance information about a distance to an object that is captured within each of the plurality of areas; and performing a classification process that classifies the plurality of areas into a plurality of groups based on the distance information, and performing a focus control process that brings a group among the plurality of groups into focus, the group that is brought into focus having an area which has been determined to be equal to or larger than a given threshold value based on area information about each of the plurality of groups.

BRIEF DESCRIPTION OF THE DRAWINGS

FIG. 4 illustrates a configuration example of an image sensor.

FIGS. 14A and 14B illustrate an effective block-null block setting example in each mode.

DESCRIPTION OF EXEMPLARY EMBODIMENTS

Figure 1:
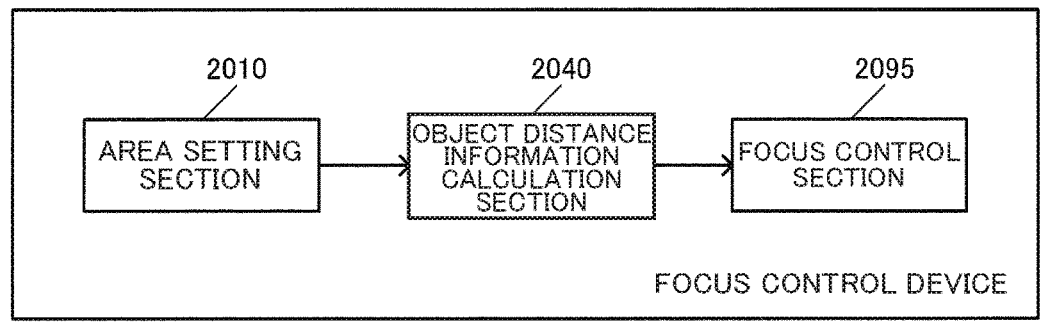
FIG. 1 illustrates a configuration example of a focus control device according to one embodiment of the invention.

According to one embodiment of the invention, there is provided a focus control device comprising:

a processor comprising hardware, the processor being configured to implement:

an area setting process that sets a plurality of areas to a captured image that has been captured by an imaging section, each of the plurality of areas including a plurality of pixels;

an object distance information calculation process that calculates distance information about a distance to an object that is captured within each of the plurality of areas; and a focus control process based on the distance information, wherein the processor implements the focus control process that performs a classification process that classifies the plurality of areas into a plurality of groups based on the distance information, and brings a group among the plurality of groups into focus, the group that is brought into focus having an area which has been determined to be equal to or larger than a given threshold value based on area information about each of the plurality of groups.

According to another embodiment of the invention, there is provided an endoscope apparatus comprising the above focus control device.

According to another embodiment of the invention, there is provided a method for controlling a focus control device comprising:

setting a plurality of areas to a captured image that has been captured by an imaging section, each of the plurality of areas including a plurality of pixels;

calculating distance information about a distance to an object that is captured within each of the plurality of areas; and performing a classification process that classifies the plurality of areas into a plurality of groups based on the distance information, and performing a focus control process that brings a group among the plurality of groups into focus, the group that is brought into focus having an area which has been determined to be equal to or larger than a given threshold value based on area information about each of the plurality of groups.

The exemplary embodiments of the invention are described below. Note that the following exemplary embodiments do not in any way limit the scope of the invention laid out in the claims. Note also that all of the elements described below in connection with the exemplary embodiments should not necessarily be taken as essential elements of the invention.

1. Method

A method used in connection with the embodiments of the invention is described below. A captured image may include an object that serves as an obstacle in addition to an object that is of interest to the user (i.e., an object to which the user is paying attention). In such a case, it is desirable that the object that is of interest to the user be easily observed (i.e., be brought into focus) within the captured image. However, the object that is of interest to the user is not necessarily brought into focus when an autofocus (AF) process is used in a simple way. For example, when a contrast AF process is used, a treatment tool may be brought into focus although the user is paying attention to tissue, since an area having high contrast is brought into focus. When a phase detection AF process is used, for example, it is possible to acquire information (e.g., lens moving amount) for achieving an in-focus state at each point at which phase difference information can be acquired. In this case, however, it is necessary to separately take account of a point that is of interest to the user.

It is possible to accurately bring the desired object into focus by utilizing a method that prompts the user to designate an object that serves as an obstacle (e.g., the method disclosed in JP-A-2006-245792). However, the state of the obstacle within the captured image may frequently change in a given situation. In such a case, since the user must designate the obstacle each time the state of the obstacle has changed, the burden imposed on the user increases.

For example, when an endoscopic procedure (e.g., laparoscopic surgery) is performed, a treatment tool is inserted into a body together with a scope (imaging section), and a treatment on tissue is performed using the treatment tool. The treatment tool is a tool that is used for the treatment on tissue. Specific examples of the treatment tool include an energy device such as an electrosurgical knife, forceps, and the like. Since the treatment tool is used for the treatment on tissue (e.g., membrane-like tissue is pulled upward using forceps, or tissue secured using forceps is excised using an electrosurgical knife), the treatment tool is frequently moved by the user (doctor or operator). Therefore, the position and the size of the treatment tool within the captured image change frequently. Specifically, since an area in which an obstacle is captured frequently changes in a case where the user is paying attention to tissue and a treatment tool serves as an obstacle, and a case where the user is paying attention to a treatment tool and tissue serves as an obstacle, the burden imposed on the user increases if the user must manually designate an obstacle.

If the object that is of interest to the user can be automatically determined within the captured image, it is possible to bring the object into focus by performing an AF process using information about an area in which the object is captured.

The invention proposes the focus control device described below. As illustrated in FIG. 1, a focus control device according to one embodiment of the invention includes an area (region) setting section 2010 that sets a plurality of areas (regions) to a captured image that has been captured by an imaging section (that corresponds to the imaging section 200 illustrated in FIG. 3 (described later)), each of the plurality of areas (regions) including a plurality of pixels, an object distance information calculation section 2040 that calculates distance information about the distance to the object that is captured within each of the plurality of areas (regions), and a focus control section 2095 that performs a focus control process based on the distance information. The focus control section 2095 performs a classification process that classifies the plurality of areas (regions) into a plurality of groups based on the distance information, and performs the focus control process based on area information about each of the plurality of groups.

It suffices that the area information be information that represents an area. The area information is not limited to an area itself. For example, when each area (each evaluation block or region) has an identical size (see FIGS. 8A and 8B), the area is information that is proportional to the number of evaluation blocks (regions). Therefore, the number of evaluation blocks (regions) classified into each group may be used as the area information about each group. The area information may represent a relative value. For example, the area information may represent an area ratio with respect to a given area. More specifically, the ratio of the area or the number of evaluation blocks (regions) classified into each group, to the area or the number of effective blocks (regions) (i.e., evaluation blocks other than null blocks or regions) (described later) may be used as the area information. The above ratio need not necessarily be calculated with respect to the effective blocks (regions). The ratio with respect to the AF area (described later), the ratio with respect to the entire captured image, or the like may be used as the area information. Note that it is desirable to change the determination standard (reference) (e.g., threshold value) that is used for the focus control process when the area (region) that is used to calculate the ratio is changed.

For example, when the method is applied to an endoscopic procedure, the captured image is an in vivo image in which a spatially restricted area is captured. It is considered that the user (e.g., scopist) operates the imaging section so that the desired object can be easily observed. For example, the user moves the imaging section so as to directly face the tissue of interest. Therefore, the object of interest (i.e., tissue) occupies a certain area within the acquired captured image. Specifically, it is likely that the object of interest occupies a large area within the captured image, and it is possible to appropriately determine the object of interest by utilizing the area information, and bring the object into focus.

The group classification process is performed based on the distance information. For example, the evaluation blocks that are close to each other as to the distance (i.e., the distance with respect to the imaging section) represented by the distance information may be classified as one group (as described in detail later).

Note that the focus control process according to the embodiments of the invention is not limited to a control process that brings a group having the largest area into focus. For example, the focus control section 2095 may perform a focus control process that preferentially brings a group among the plurality of groups that is situated away from the imaging section into focus.

The expression "preferentially brings a group that is situated away from the imaging section into focus" used herein means that, when the captured image includes a first group that is situated at a distance D1 from the imaging section 200, and a second group that is situated at a distance D2 (<D1) from the imaging section 200, for example, it is likely that the first group is brought into focus as compared with the second group. Since the method according to the embodiments of the invention calculates the distance information about each area, it is also possible to calculate the distance information about each group. Specifically, the above control process can be implemented by a comparison process that compares the distance information calculated on a group basis.

This makes it possible to bring an appropriate object into focus when it is likely that the user is paying attention to an object that is situated away from the imaging section 200. As described above, it is considered that tissue (i.e., object of interest) occupies a certain area within the captured image, and it is unlikely that an object other than the tissue lies behind the tissue (so as to be situated further away from the imaging section 200). Specifically, the object of interest is situated farthest (or almost farthest) within the captured image. Since the user performs an endoscopic procedure while observing the captured image, a treatment tool or the like that serves as an obstacle may be captured in front of the tissue (so as to be situated closer to the imaging section 200). However, since the tissue is preferentially brought into focus instead of the treatment tool, it is possible to prevent a situation in which the treatment tool is brought into focus.

Although it is likely that an object that is situated farthest (situated at the deepest position) is the object of interest to the user when the focus control device according to the embodiments of the invention is used (see above), the user may pay attention to another object. For example, when the user performs suture, the user must hold a needle and a suture at an appropriate angle using forceps or the like. In this case, the user normally pays attention to the needle and the suture that are situated in front of the tissue, instead of the tissue.

Specifically, the focus control process according to the embodiments of the invention basically preferentially brings an area that is situated away from the imaging section 200 into focus while using the area information, but may be performed according to a different principle when an exception condition has been satisfied. For example, a needle and a suture may be brought into focus by bringing an object that is situated close to the imaging section 200 into focus.

The embodiments of the invention are described in detail below. The focus control device according to the embodiments of the invention, and a system configuration example of an endoscope apparatus that includes the focus control device will be described first, and the flow of the process according to the embodiments of the invention will then be described using flowcharts. A specific example according to the embodiments of the invention will be described thereafter, and a modification will then be described.

2. System Configuration Example

Figure 3:
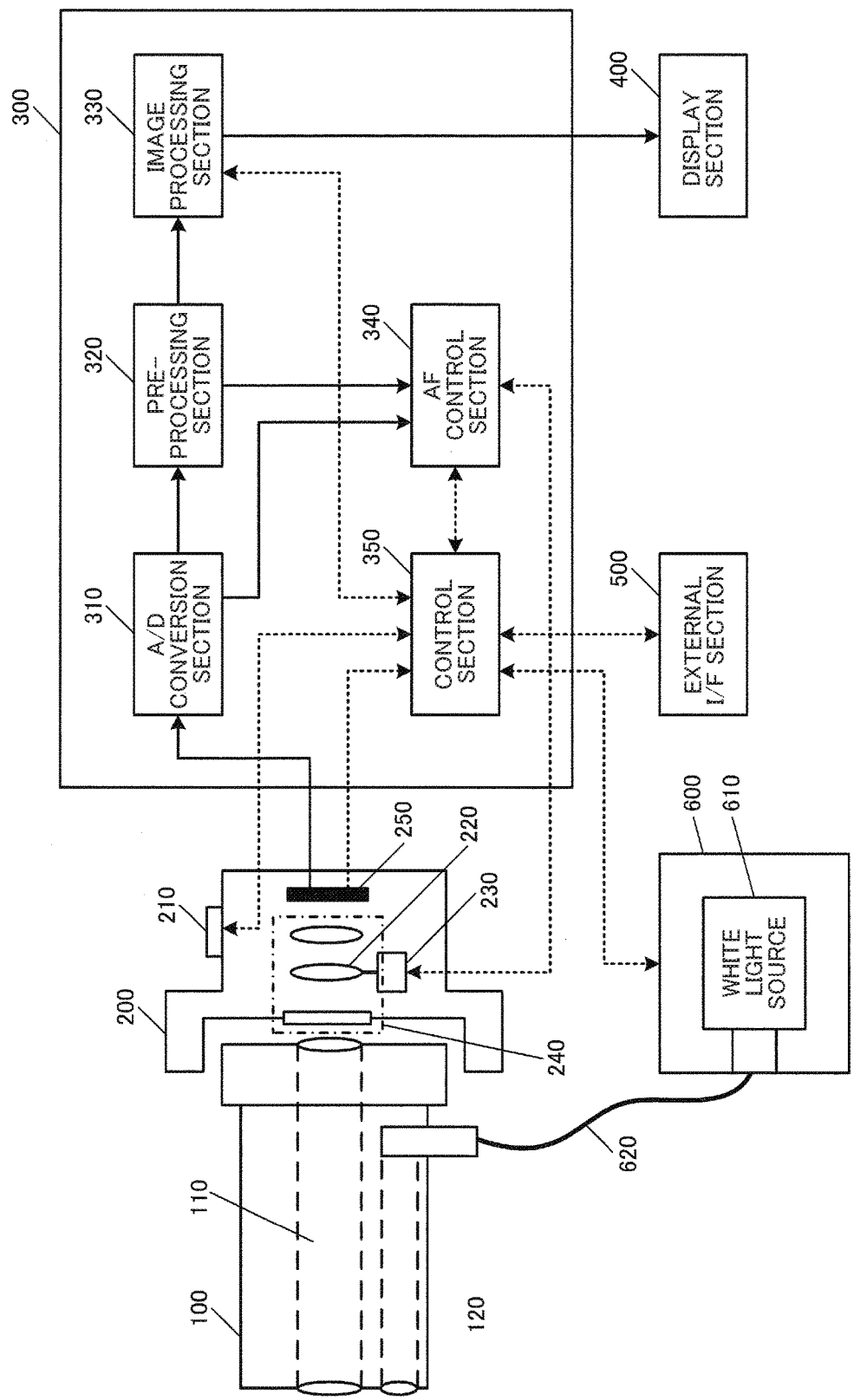
FIG. 3 illustrates a configuration example of an endoscope apparatus that includes a focus control device according to one embodiment of the invention.

An endoscope apparatus (endoscope system) according to one embodiment of the invention is described below with reference to FIG. 3. The endoscope system according to one embodiment of the invention includes a rigid scope 100 that is inserted into a body, an imaging section 200 that is connected to the rigid scope 100, a processing section 300, a display section 400, an external I/F section 500, and a light source section 600.

The light source section 600 includes a white light source 610 that emits white light, and a light guide cable 620 that guides the light emitted from the white light source 610 to the rigid scope.

The rigid scope 100 includes a lens system 110 that includes an imaging lens, a relay lens, an eyepiece, and the like, and a light guide section 120 that guides the light emitted from the light guide cable 620 to the end of the rigid scope.

The imaging section 200 includes an objective lens system 240 that forms an image of the light emitted from the lens system 110. The objective lens system 240 includes a focus lens 220 that adjusts the in-focus object plane position. The imaging section 200 also includes an image sensor 250 that photoelectrically converts the reflected light focused by the objective lens system 240 to generate an image, a focus lens driver section 230 that drives the focus lens 220, and an AF button (AF start/stop button) 210 that controls AF start/stop. The focus lens driver section 230 is implemented by a voice coil motor (VCM), for example.

The details of the image sensor 250 according to one embodiment of the invention are described below with reference to FIG. 4. FIG. 4 is a partially enlarged view illustrating the image sensor 250. As illustrated in FIG. 4, the image sensor 250 has a structure in which a plurality of pixels are arranged in a two-dimensional array, and R, G, and B color filters are disposed in a Bayer array on a pixel basis. Some of the pixels are provided with a phase sensor in which the opening is partially shielded. The phase sensors include a phase sensor S1 group and a phase sensor S2 group that differ as to the placement of the shielding area.

For example, the phase sensor S1 group has a configuration in which the right side of the opening is shielded, and receives light that is incident on the left side of the opening. The phase sensor S2 group has a configuration in which the left side of the opening is shielded, and receives light that is incident on the right side of the opening. According to this configuration, it is possible to obtain an effect similar to that obtained when the pupil of the objective lens system 240 is divided into a right area and a left area. Therefore, signals from the phase sensor S1 group and signals from the phase sensor S2 group are considered to be phase signals with respect to a light ray that has passed through each pupil. For example, when the position of the object image formed by the objective lens system 240 coincides with the image plane of the image sensor 250 (i.e., the object is in focus), the phase signals output from the phase sensor S1 group coincide with the phase signals output from the phase sensor S2 group. When the position of the object image formed by the objective lens group 240 is situated in front of, or behind, the image plane of the image sensor 250 (i.e., the object is out of focus), a phase difference occurs between the phase signals output from the phase sensor S1 group and the phase signals output from the phase sensor S2 group. The placement of the shielding area may be modified in various ways (e.g., the shielding area may be placed on the upper side, or may be placed on the lower side, or may be placed diagonally) so that the phase difference in the direction corresponding to the placement can be detected.

When a phase sensor is provided to an image sensor having a Bayer array, it is preferable to provide the phase sensor to some of the R pixels (see FIG. 4) since tissue that that is observed using an endoscope system has a relatively large amount of information in the G channel and the B channel. It is preferable to provide the phase sensor S1 group and the phase sensor S2 group to be situated close to each other within the image sensor 250. It is preferable to provide the phase sensor S1 group and the phase sensor S2 group so as not to be situated adjacent to each other taking account of the quality of the image obtained by capturing the object using the image sensor 250.

The image sensor 250 may be an arbitrary image sensor other than an image sensor having a Bayer color filter array (see FIG. 4), such as an image sensor that utilizes a complementary color filter, a stacked image sensor that is designed so that each pixel can receive light having a different wavelength without using a color filter, and a monochrome image sensor that does not utilize a color filter, as long as the object can be captured to obtain an image.

A dedicated sensor that is provided with the phase sensor S1 group and the phase sensor S2 group may be provided separately instead of providing the phase sensor S1 group and the phase sensor S2 group to some of the pixels of the image sensor 250 (see FIG. 4). The dedicated sensor may be placed on the same optical axis as the image sensor 250, or may be placed on a different optical axis using a semi-transparent mirror or the like.

The processing section 300 includes an A/D conversion section 310, a pre-processing section 320, an image processing section 330, an AF control section 340, and a control section 350. The A/D conversion section 310 converts an analog signal sequentially output from the image sensor 250 into a digital image, and sequentially outputs the digital image to the pre-processing section 320 and the AF control section 340. The pre-processing section 320 performs image processing (e.g., white balance process and interpolation process (demosaicing process)) on the image output from the AD conversion section 310, and sequentially outputs the resulting image to the image processing section 330 and the AF control section 340. The size of the image output from the pre-processing section 320 is the same as the size of the image that is output from the A/D conversion section 310 to the AF control section 340. The image processing section 330 performs image processing (e.g., color conversion process, grayscale transformation process, edge enhancement process, scaling process, and noise reduction process) on the image output from the pre-processing section 320, and sequentially outputs the resulting image to the display section 400.

The AF control section 340 includes an area setting section (AF area setting section) 2010, a mode setting section 2020, a phase signal generation section 2030, an object distance information calculation section 2040, a reliability calculation section 2050, an object feature quantity calculation section 2060, an area-of-interest estimation section 2070, and a lens destination determination section 2080.

The area setting section 2010 sets a plurality of areas used for the AF process to the captured image. The plurality of areas may include both an AF area and an evaluation block. The mode setting section 2020 sets an AF mode. The phase signal generation section 2030 generates a phase signal (phase difference signal in a narrow sense) based on a sensor signal from the phase sensor. The object distance information calculation section 2040 calculates distance information on an evaluation block basis based on the generated phase difference signal, the distance information representing the distance to the captured object. The reliability calculation section 2050 calculates reliability on an evaluation block basis, the reliability representing the probability that the calculated distance information is reliable. The object feature quantity calculation section 2060 calculates a feature quantity from the captured image. The feature quantity may be calculated on an evaluation block basis. The area-of-interest estimation section 2070 estimates an area of interest that is an area within the captured image that is determined to be of interest to the user (i.e., an area to which the user is paying attention). The area of interest may represent the group described later, or may represent one area (evaluation block) within the group. The lens destination determination section 2080 determines the destination of the focus lens 220 based on the area-of-interest estimation result.

Figure 5:
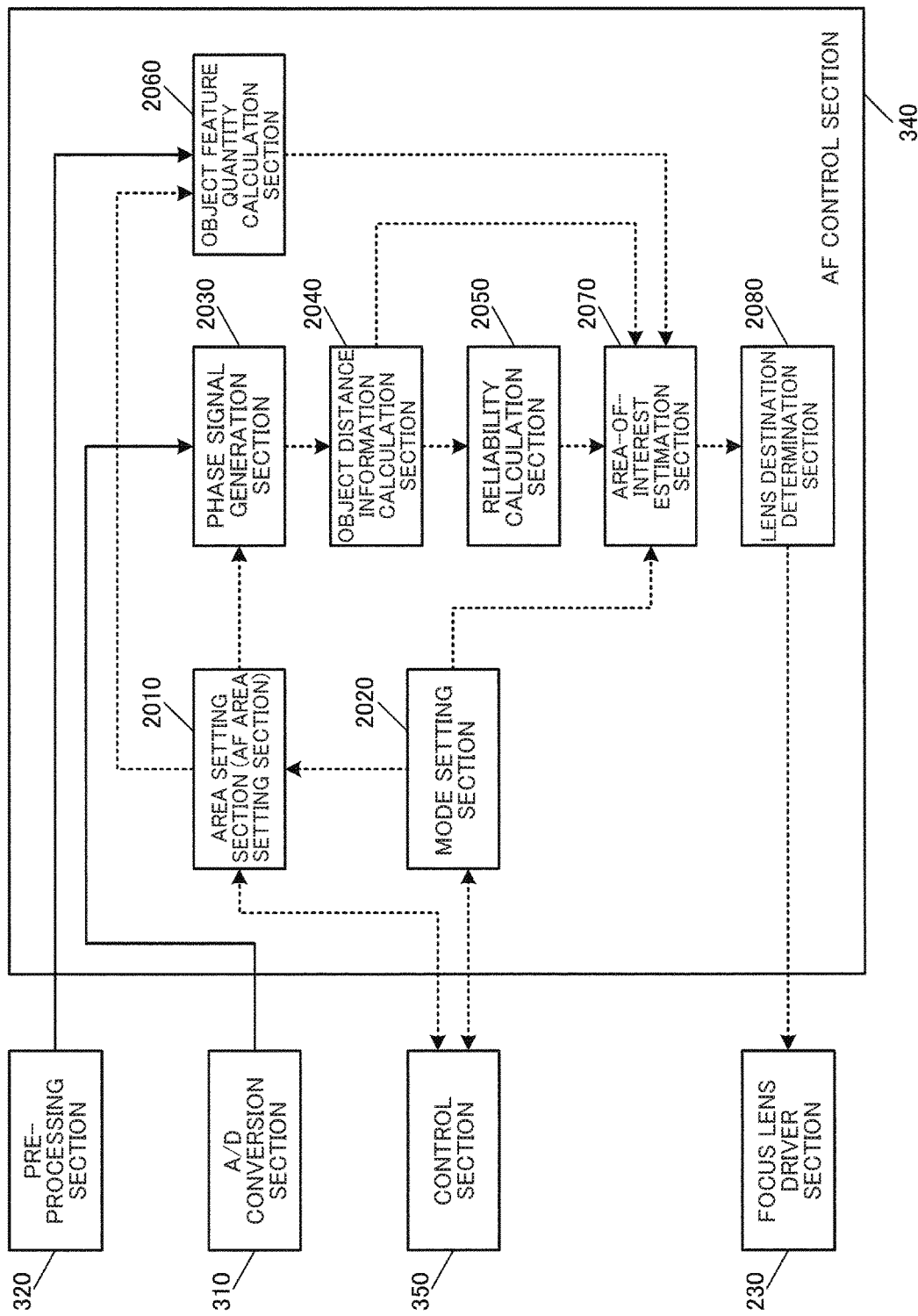
FIG. 5 illustrates a configuration example of an AF control section.

Note that the details of the process performed by each section of the AF control section 340 are described later. The focus control section 2095 illustrated in FIG. 1 may correspond to the configuration of the AF control section 340 illustrated in FIG. 5 excluding the area setting section 2010 and the object distance information calculation section 2040, for example. The focus control device according to one embodiment of the invention may correspond to the AF control section 340 illustrated in FIG. 5. Note that the configuration of the focus control device is not limited thereto. Various modifications and variations may be made (e.g., the entire processing section 300 illustrated in FIG. 1 may be used as the focus control device). Some of the elements included in the focus control device may be omitted, or an additional element may be provided to the focus control device, for example. Various modifications and variations may also be made of the configuration illustrated in FIG. 3 and the like.

The control section 350 is bidirectionally connected to the external I/F section 500, the image processing section 330, the AF control section 340, the image sensor 250, the AF button 210, and the like, and exchanges a control signal with the external I/F section 500, the image processing section 330, the AF control section 340, the image sensor 250, the AF button 210, and the like.

The display section 400 is a liquid crystal monitor, for example. The display section 400 displays the image sequentially output from the image processing section 330.

The external I/F section 500 is an interface that allows the user to perform an input operation and the like on the endoscope apparatus. For example, the external I/F section 500 includes a mode button that is used to switch the AF mode, a setting button that is used to set the position and the size of the AF area, an adjustment button that is used to adjust the parameter of image processing, and the like. The endoscope system according to one embodiment of the invention has a tissue mode (i.e., AF mode) in which tissue is brought into focus, and a needle-suture mode (i.e., AF mode) in which a needle and a suture used for an endoscopic procedure are brought into focus.

3. Process Flow

An outline of the AF control process that is performed by the AF control section 340 according to one embodiment of the invention is described below with reference to FIG. 6 and the like. The process illustrated in FIG. 7 (flowchart) will be described as a comparative example with respect to one embodiment of the invention, problems that may occur when the process illustrated in FIG. 7 is used will be described thereafter, and the focus control process according to one embodiment of the invention that can solve the problems will then be described with reference to FIG. 13 (flowchart).

Figure 6:
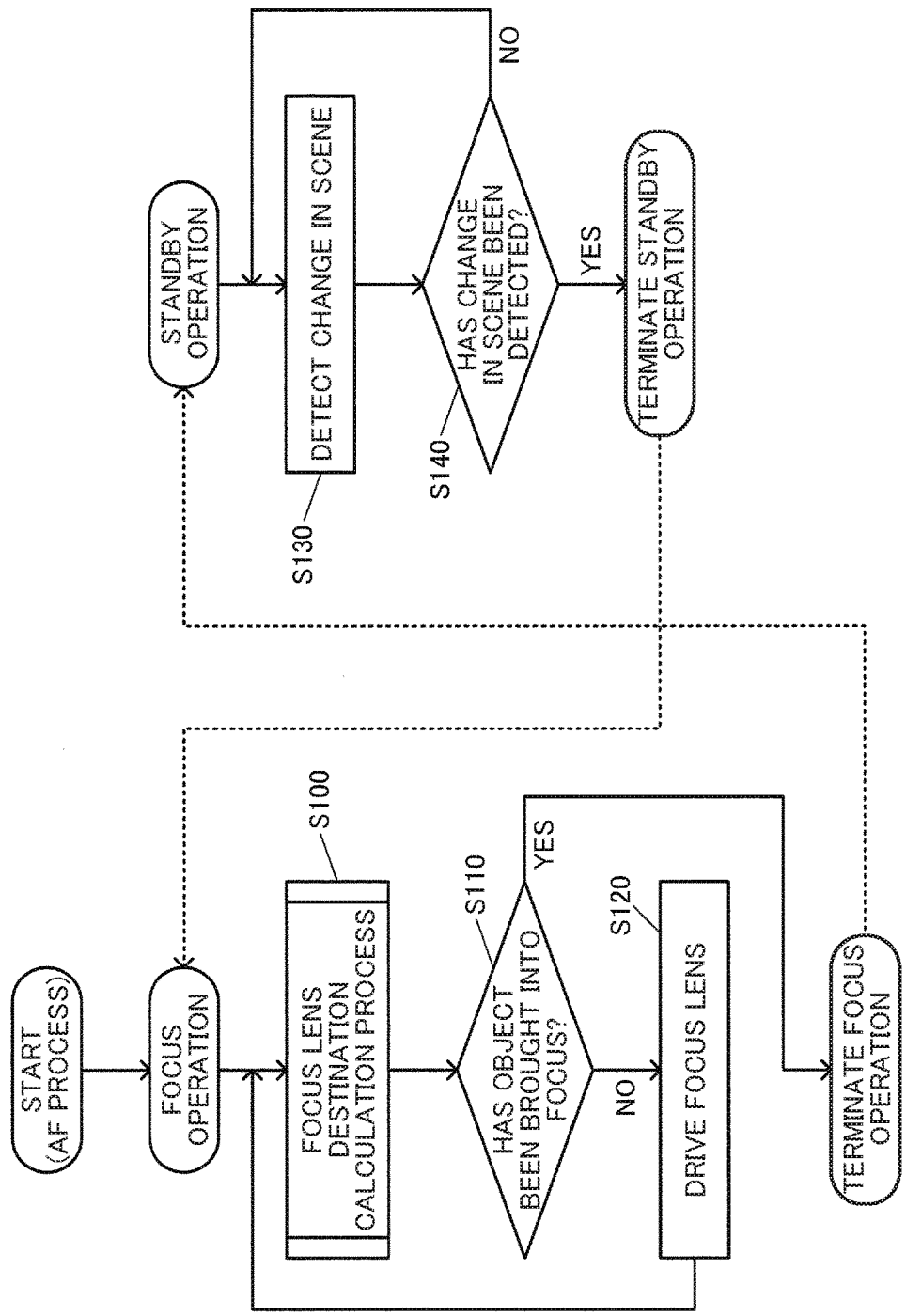
FIG. 6 is a flowchart illustrating a focus control process according to one embodiment of the invention.
Figure 7:
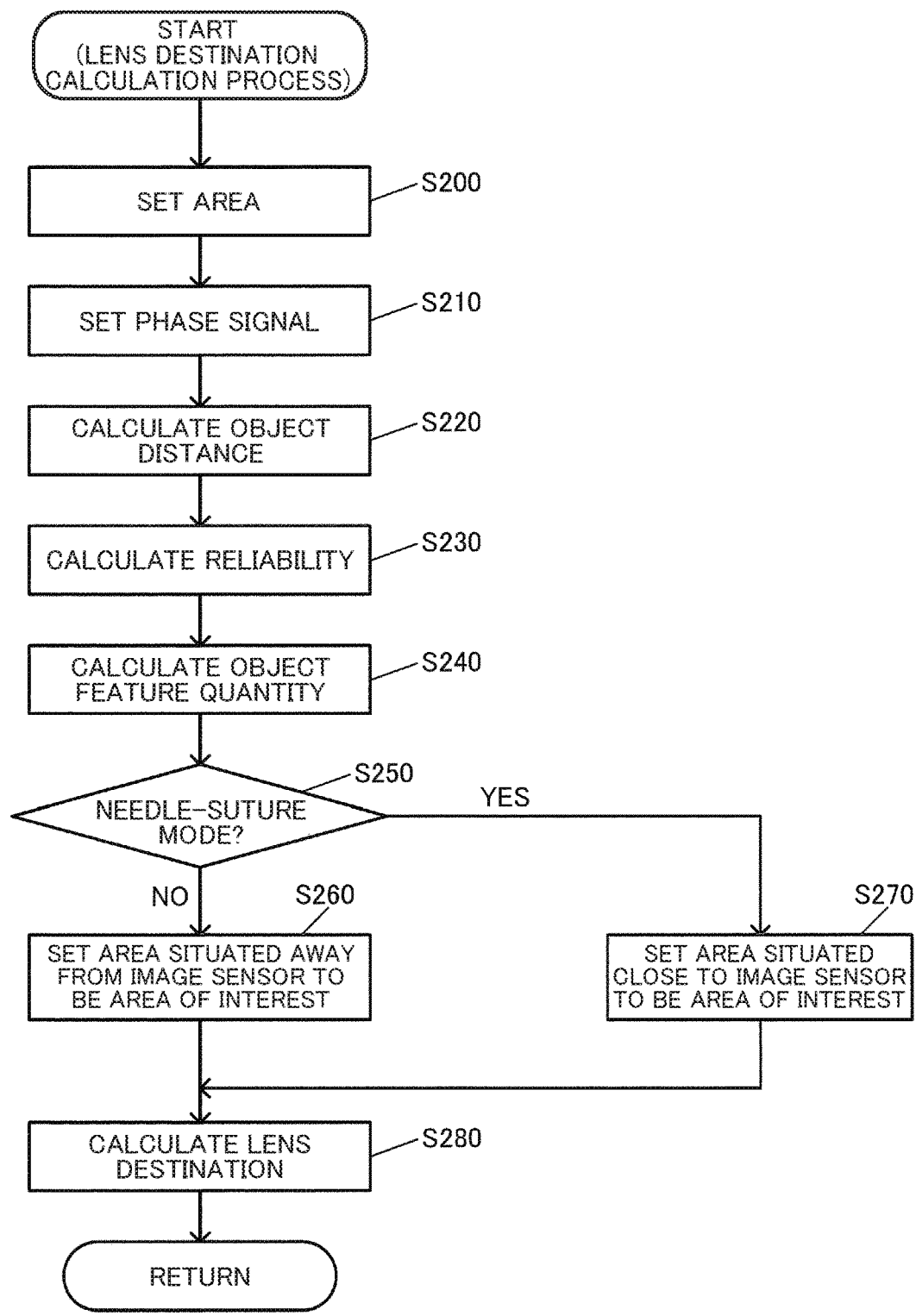
FIG. 7 is a flowchart illustrating a lens destination calculation process according to a comparative example.

As illustrated in FIG. 6, when the user has operated the AF button 210 to start the AF process, the AF control section 340 starts a focus operation. The AF control section 340 calculates the destination of the focus lens 220 based on the image sequentially output from the A/D conversion section 310 (S100). The details of the focus lens destination calculation process (S100) are described later. The AF control section 340 determines whether or not the object has been brought into focus (S110). More specifically, the AF control section 340 determines whether or not the destination of the focus lens 220 that has been calculated by the step S100 lies within a given range (within a given error determined taking account of the depth of field and the like) with respect to the current position of the focus lens 220, and determines that the object has been brought into focus when the destination of the focus lens 220 lies within the given range. Note that the AF control section 340 may determine whether or not the object has been brought into focus by performing a known in-focus determination process or the like.

When the AF control section 340 has determined that the object has not been brought into focus, the AF control section 340 instructs the focus lens driver section 230 to drive the focus lens 220 based on the destination of the focus lens 220 calculated by the step S100 (S120). The AF control section 340 then performs the step S100. When the AF control section 340 has determined that the object has been brought into focus in the step S110, the AF control section 340 terminates the focus operation.

In one embodiment of the invention, the destination of the focus lens 220 is calculated using the phase difference as described later. When noise is not added to the phase signal (as described later), the object can be brought into focus when the destination of the focus lens 220 has been calculated only once. However, since noise is superimposed on the phase signal in the actual situation, it may be impossible to bring the object into focus when the destination of the focus lens 220 has been calculated only once. Therefore, the steps S100 to S120 are repeated until the calculated destination of the focus lens 220 lies within a given range with respect to the current position of the focus lens 220.

When the AF control section 340 has terminated the focus operation, the AF control section 340 starts a standby operation. Specifically, the AF control section 340 detects a change in scene (S130). The AF control section 340 detects a change in scene by monitoring a change in the color or the brightness of an image, the motion of an image, and the like using the image sequentially output from the pre-processing section 320, for example. The AF control section 340 determines whether or not a change in scene has been detected (S140). When a change in scene has not been detected, the AF control section 340 performs the step S130 again. When a change in scene has been detected, the AF control section 340 terminates the standby operation. When the AF control section 340 has terminated the standby operation, the AF control section 340 resumes the focus operation. Note that the AF control section 340 fixes the focus lens position at a position when the focus operation has been terminated (i.e., does not drive the focus lens 220) during the standby operation, for example. Note that the flow illustrated in FIG. 6 may be terminated when the user has operated the AF button 210 during the standby operation, for example.

A comparative example with respect to the focus lens destination calculation process (S100) performed by the AF control section 340 is described below with reference to FIG. 7.

In one embodiment of the invention, the tissue mode and the needle-suture mode are provided as the AF mode. For example, the control section 350 sets the AF mode to the mode setting section 2020 corresponding to information input from the external I/F section 500. The image data (captured image) that has been captured by the image sensor 250 may be analyzed by the control section 350, and the AF mode may be changed based on a specific image pattern, motion, and the like. The mode setting section 2020 outputs AF mode information that represents the tissue mode or the needle-suture mode to the area setting section 2010 and the area-of-interest estimation section 2070.

Figure 8A:
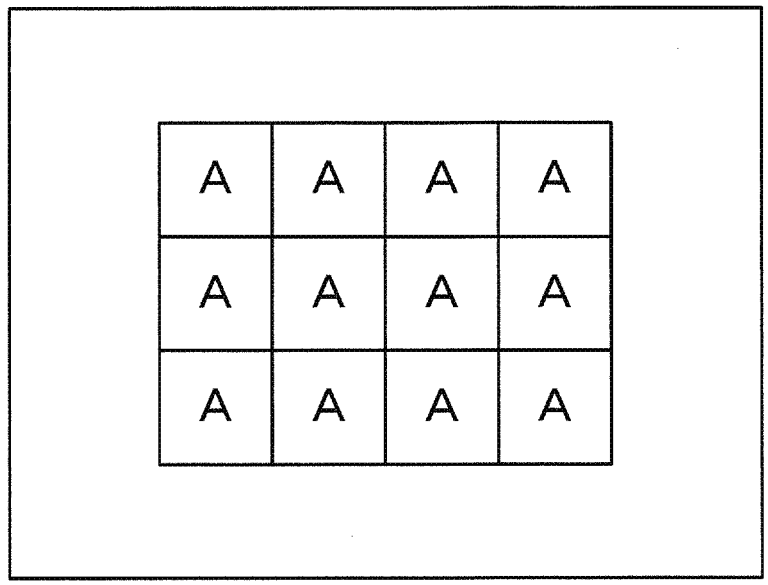
FIGS. 8A and 8B are views illustrating an area setting example corresponding to a mode.
Figure 8B:
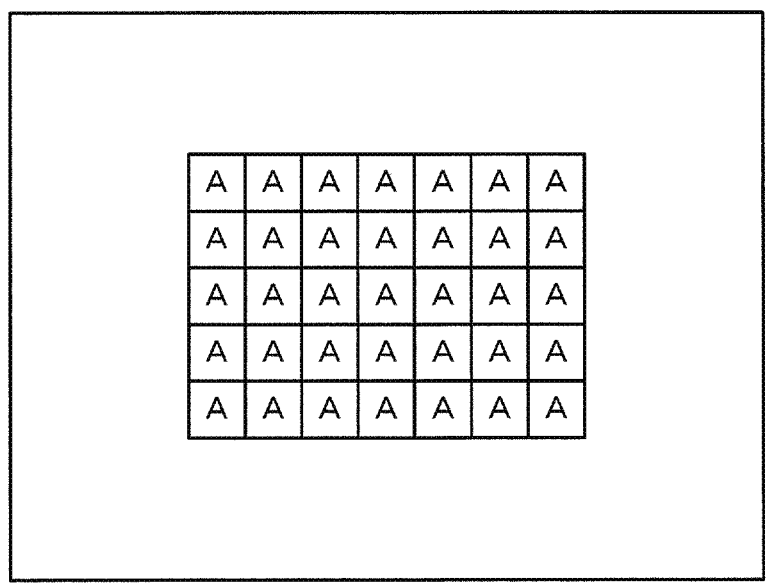

The area setting section 2010 sets an AF area that includes a plurality of blocks to the image based on information (e.g., information about the position and the size of the AF area) output from the control section 350 (S200). The area setting section 2010 outputs the AF area information to the phase signal generation section 2030 and the object feature quantity calculation section 2060. FIGS. 8A and 8B illustrate an AF area setting example. In the example illustrated in FIGS. 8A and 8B, the outer rectangle represents the entire image, and each rectangle indicated by A represents an evaluation block that is an area for which the AF evaluation value, the reliability, and the like are calculated (as described later). In the example illustrated in FIGS. 8A and 8B, the AF area is a range that includes all of the evaluation blocks. In the example illustrated in FIG. 8A, twelve (4×3) evaluation blocks are set to a center area of the image (image data). In the example illustrated in FIG. 8B, thirty-five (7×5) evaluation blocks are set to a center area of the image.

When the AF mode has been set to the tissue mode, the area setting section 2010 sets the evaluation blocks as illustrated in FIG. 8A corresponding to the AF mode information output from the mode setting section 2020. When the AF mode has been set to the needle-suture mode, the area setting section 2010 sets the evaluation blocks as illustrated in FIG. 8B so as to be smaller than those set in the tissue mode since the target object (i.e., needle and suture) is smaller than tissue. Since a needle and a suture are normally manipulated in a center area of the screen, the AF area is set to be smaller than that set in the tissue mode. Since a needle and a suture are normally captured at a position lower to some extent than the center of the image due to the effect of gravity, the evaluation blocks may be set at a position lower than the center of the image (image data) instead of setting the AF area in a center area of the image (image data) (see FIG. 8B) so that an area that includes a needle and a suture is reliably included within the AF area.

The AF area is set to an area in which it is considered that the main object is mainly captured. Each evaluation block includes at least part of the phase sensor S1 group and part of the phase sensor S2 group. The evaluation blocks need not necessarily be contiguous to each other, and may differ in size, shape, and the like. The size, the shape, and the like of the evaluation blocks may be appropriately changed corresponding to the object, the operation performed by the user, and the like. The evaluation blocks need not necessarily be changed corresponding to the mode. For example, identical evaluation blocks may be set in the tissue mode and the needle-suture mode.

The phase signal generation section 2030 generates the phase signal on an evaluation block basis based on the image output from the A/D conversion section 310 and the AF area information output from the area setting section 2010 using the pixel values that correspond to the phase sensor S1 group and the phase sensor S2 group included in each evaluation block (S210). The phase signal generation section 2030 outputs the phase signal with respect to each evaluation block to the object distance information calculation section 2040.

The object distance information calculation section 2040 calculates the distance information (object distance) about each evaluation block based on the phase signal with respect to each evaluation block output from the phase signal generation section 2030 (S220). The object distance information calculation section 2040 outputs the calculated distance information about each evaluation block to the area-of-interest estimation section 2070. The object distance information calculation section 2040 outputs the degree of correlation of the phase signal (described later) with respect to each evaluation block to the reliability calculation section 2050. The term "distance information" used herein refers to the distance from the image plane to the object captured within each area. Note that the object distance is not limited to a distance in a strict sense, but may be information from which the positional relationship of the object in the forward-backward direction can be determined. For example, the position of the focus lens 220 or the like may be used as the distance information. The reference position for the distance information is not limited to the image plane. Another position such as the end of the rigid scope 100 may also be used as the reference position.

Figure 9:
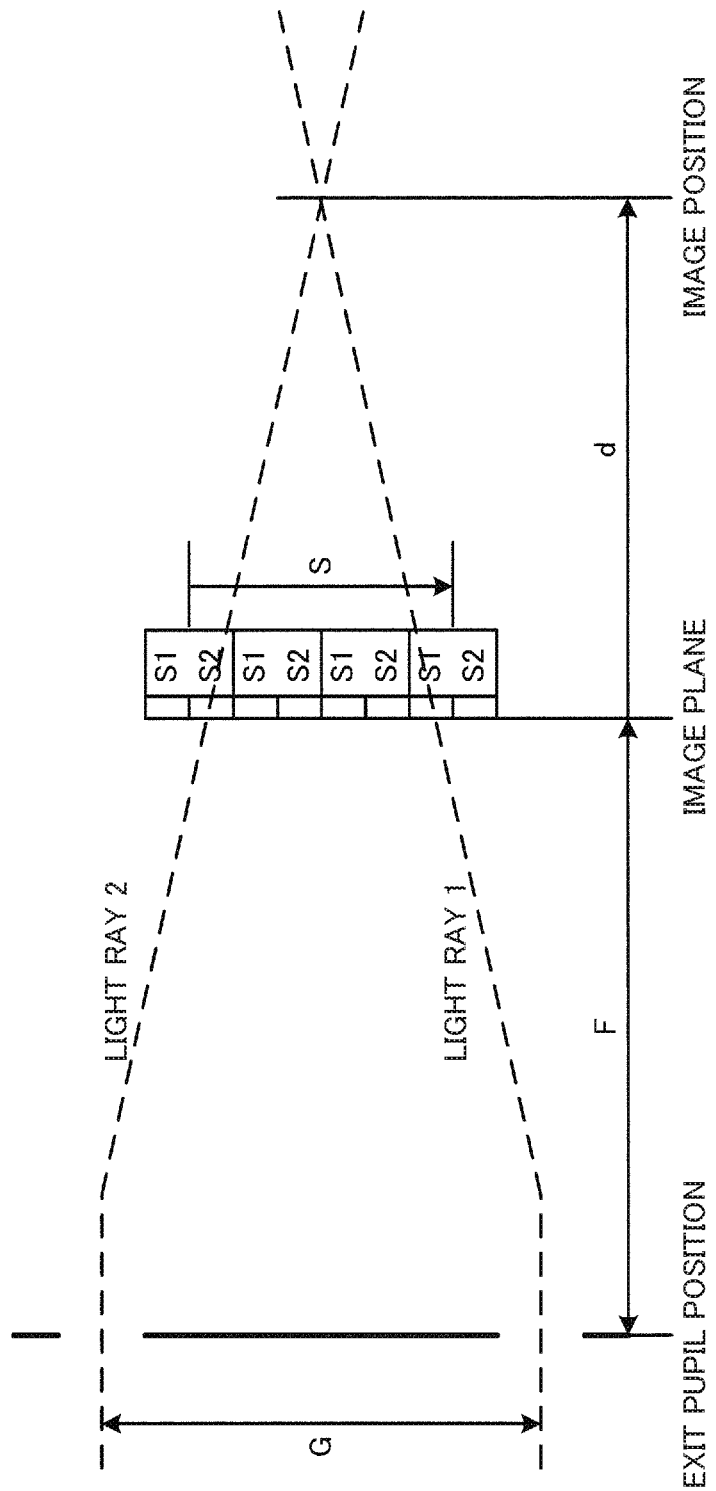
FIG. 9 is a view illustrating a method that calculates distance information from phase difference information.

The distance information calculation method that is implemented by the object distance information calculation section 2040 is described below with reference to FIG. 9. FIG. 9 is a view illustrating light rays that pass through divided pupils when the image position is situated behind the image plane. A light ray 1 is a light ray that has passed through the pupil that corresponds to the phase sensor S1 group, and a light ray 2 is a light ray that has passed through the pupil that corresponds to the phase sensor S2 group. Since the image position is situated at a position differing from the image plane (i.e., situated behind the image plane), a phase difference S occurs between the phase signals output from the phase sensor S1 group and the phase signals output from the phase sensor S2 group. Note that S is a positive or negative vector. The direction indicated by the arrow in FIG. 9 is the positive direction. The phase difference S may be determined by calculating the correlation between the phase signals using known phase detection AF technology while gradually shifting the phase signals output from the phase sensor S1 group and the phase signals output from the phase sensor S2 group, and calculating the phase difference S from the position at which the correlation becomes a maximum, for example. The distance between the image plane and the exit pupil is referred to as F, the distance between the centers of gravity of the divided pupils is referred to as G, and the defocus amount is referred to as d. Note that d is a positive or negative vector. The direction indicated by the arrow in FIG. 9 is the positive direction. In this case, the following expression (1) is satisfied, and the defocus amount d can be calculated using the following expression (2) obtained by transforming the expression (1). Note that the above description is similarly applied to the case where the image position is situated in front of the image plane.

$$G/(F+d)=S/d \tag{1}$$

$$d=F \cdot S/(G-S) \tag{2}$$

When the defocus amount d from the image plane has been calculated, the object distance can be calculated from the design data of an optical system obtained by combining the lens system 110 of the rigid scope 100 and the objective lens system 240. For example, a look-up table that links the defocus amount d and the object distance may be provided in advance, and the object distance may be calculated using the look-up table.

The reliability calculation section 2050 calculates the reliability that is a measure that represents the probability that the object distance calculated on an evaluation block basis is reliable (S230). For example, the degree of correlation of the phase signal with respect to each evaluation block output from the object distance information calculation section 2040 is used as the reliability. The reliability decreases as the amount of noise due to the image sensor 250, the A/D conversion section 310, and the like increases, and increases as the amount of noise decreases. The reliability increases as the contrast of the object increases. The reliability calculation section 2050 outputs the reliability with respect to each evaluation block to the area-of-interest estimation section 2070.

The object feature quantity calculation section 2060 calculates the object feature quantity with respect to each evaluation block based on the image output from the pre-processing section 320 (S240). The object feature quantity is a quantity that characterizes the object captured within each evaluation block. For example, the object feature quantity is color information about each evaluation block. The object feature quantity calculation section 2060 outputs the calculated object feature quantity to the area-of-interest estimation section 2070. The image used to calculate the object feature quantity may be the image output from the A/D conversion section 310.

The object feature quantity may be an arbitrary feature quantity (e.g., the brightness, the edge quantity, the temperature of the object obtained from a dedicated sensor (not illustrated in the drawings), and the reflectivity with respect to narrow-band light) as long as at least whether or not the object is tissue can be determined.

The area-of-interest estimation section 2070 determines whether or not the AF mode output from the mode setting section 2020 is the needle-suture mode (S250). For example, the control section 350 sets the AF mode to the mode setting section 2020 corresponding to information input from the external I/F section 500. The image data that has been captured by the image sensor 250 may be analyzed by the control section 350, and the AF mode may be changed based on a specific image pattern, motion, and the like.

When the AF mode has been set to a mode other than the needle-suture mode (i.e., when the AF mode has been set to the tissue mode) (i.e., when the user is paying attention to tissue), the area-of-interest estimation section 2070 sets the evaluation block that is estimated to be tissue to be the area of interest (S260). When an endoscopic procedure is performed using an in vivo image or the like, it is likely that tissue (i.e., the object of interest) is situated away from the image sensor 250 in terms of the object distance (see above). Therefore, the area-of-interest estimation section 2070 sets an evaluation block for which the object distance represents a position that is farthest from the image sensor 250, the object feature quantity represents tissue, and the reliability is equal to or larger than a given value (i.e., an evaluation block that is reliable at least to a certain extent), to be the area of interest based on the object distance, the reliability, the color information, and the like with respect to each evaluation block, for example. The area-of-interest estimation section 2070 outputs the area of interest that has been set as described above to the lens destination determination section 2080. Although an example in which the object feature quantity and the reliability are used to improve the focus accuracy has been described above, the object feature quantity and the reliability need not necessarily be used.

When the AF mode has been set to the needle-suture mode (i.e., when the user is paying attention to a needle, a suture, and a treatment tool (e.g., forceps) that holds the needle and the suture), the area-of-interest estimation section 2070 sets the evaluation block that is estimated to be such an object to be the area of interest (S270). When an endoscopic procedure is performed, a needle and a suture are normally manipulated using a treatment tool (e.g., forceps) at a position in front of tissue. Therefore, the area-of-interest estimation section 2070 sets an evaluation block for which the object distance represents a position that is nearest to the image sensor 250, and the reliability is equal to or larger than a given value, to be the area of interest based on the object distance, the reliability, the color information, and the like with respect to each evaluation block, for example. The area-of-interest estimation section 2070 outputs the area of interest that has been set as described above to the lens destination determination section 2080. Although an example in which the reliability is used to improve the focus accuracy has been described above, the reliability need not necessarily be used. The object feature quantity may be used in addition to, or instead of, the reliability.

The lens destination determination section 2080 determines the destination of the focus lens 220 based on the area of interest output from the area-of-interest estimation section 2070 (S280). For example, the destination of the focus lens 220 may be determined based on the defocus amount d that corresponds to the evaluation block set to be the area of interest. The lens destination determination section 2080 may adjust the destination of the focus lens 220 corresponding to the AF mode, the distribution of the object distance with respect to each evaluation block, the distribution of the object feature quantity, and the like.

Figure 10:
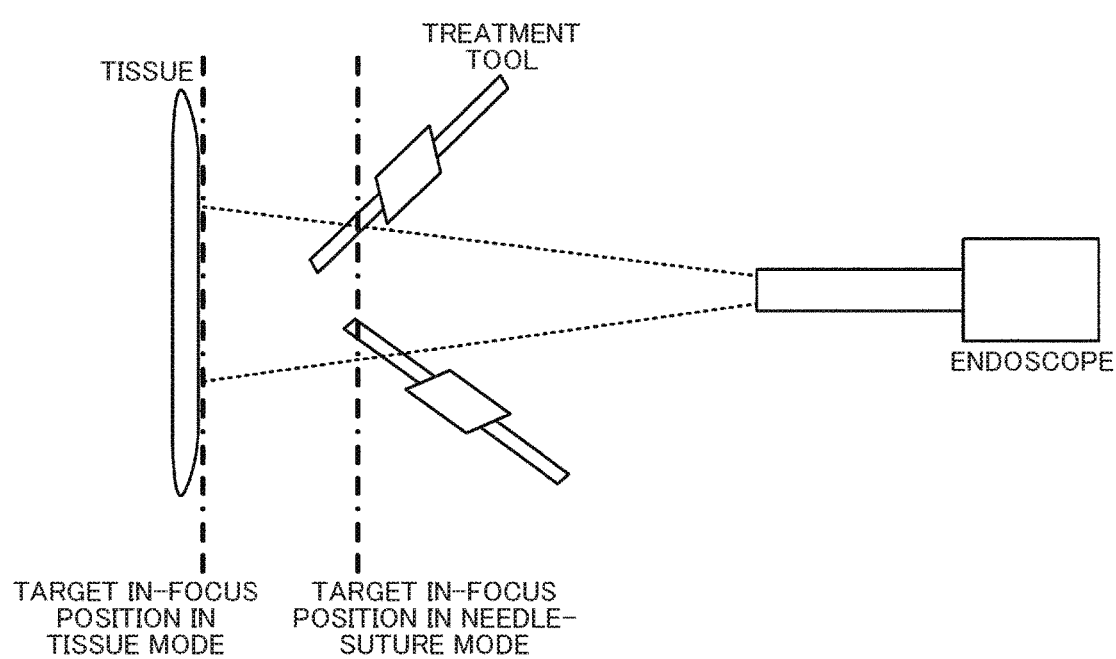
FIG. 10 is a view illustrating the relationship between the relative positional relationship between a plurality of objects and an imaging section, and a target in-focus position.

FIG. 10 illustrates an example of the object that is observed using an endoscope. The main object that is observed using an endoscope is tissue and a treatment tool. The tissue is normally situated at a position away from the endoscope, and the treatment tool is operated by the user, and is placed at an arbitrary position between the endoscope and the tissue. The dotted lines indicate the range that can be captured within the AF area. In the tissue mode, the tissue that is situated away from the endoscope is set to be the target in-focus position. In the needle-suture mode, the end of a treatment tool (e.g., forceps) that holds a needle and a suture, and is situated at the same object distance as that of the tissue, or situated at an object distance closer to the endoscope as compared with the tissue, is set to be the target in-focus position.

According to the process illustrated in FIG. 7, since an area that is situated away from the image sensor 250 is set to be the area of interest in the tissue mode, the tissue can be brought into focus. Since an area that is situated close to the image sensor 250 is set to be the area of interest in the needle-suture mode, the end of the treatment tool can be brought into focus.

According to the method described above, it is possible to bring the object of interest into focus without requiring the user to perform a complex operation by estimating the object of interest using the object distance with respect to each of a plurality of evaluation blocks, and driving the focus lens based on the estimation results. When the AF mode has been set to the needle-suture mode, it is possible to bring the object of interest into focus while preventing a situation in which tissue is necessarily brought into focus, by changing the evaluation block setting method, and estimating an area that is of interest to the user in a different way. It is possible to implement a stable AF control process without being affected by noise, the contrast of the object, and the like, by calculating the reliability with respect to each evaluation block, and utilizing an evaluation block having a reliability equal to or larger than a given value. It is possible to more accurately bring tissue into focus in the tissue mode, and bring an object other than tissue into focus in the needle-suture mode, by determining whether or not the object captured within each evaluation block is tissue.

Figure 11:
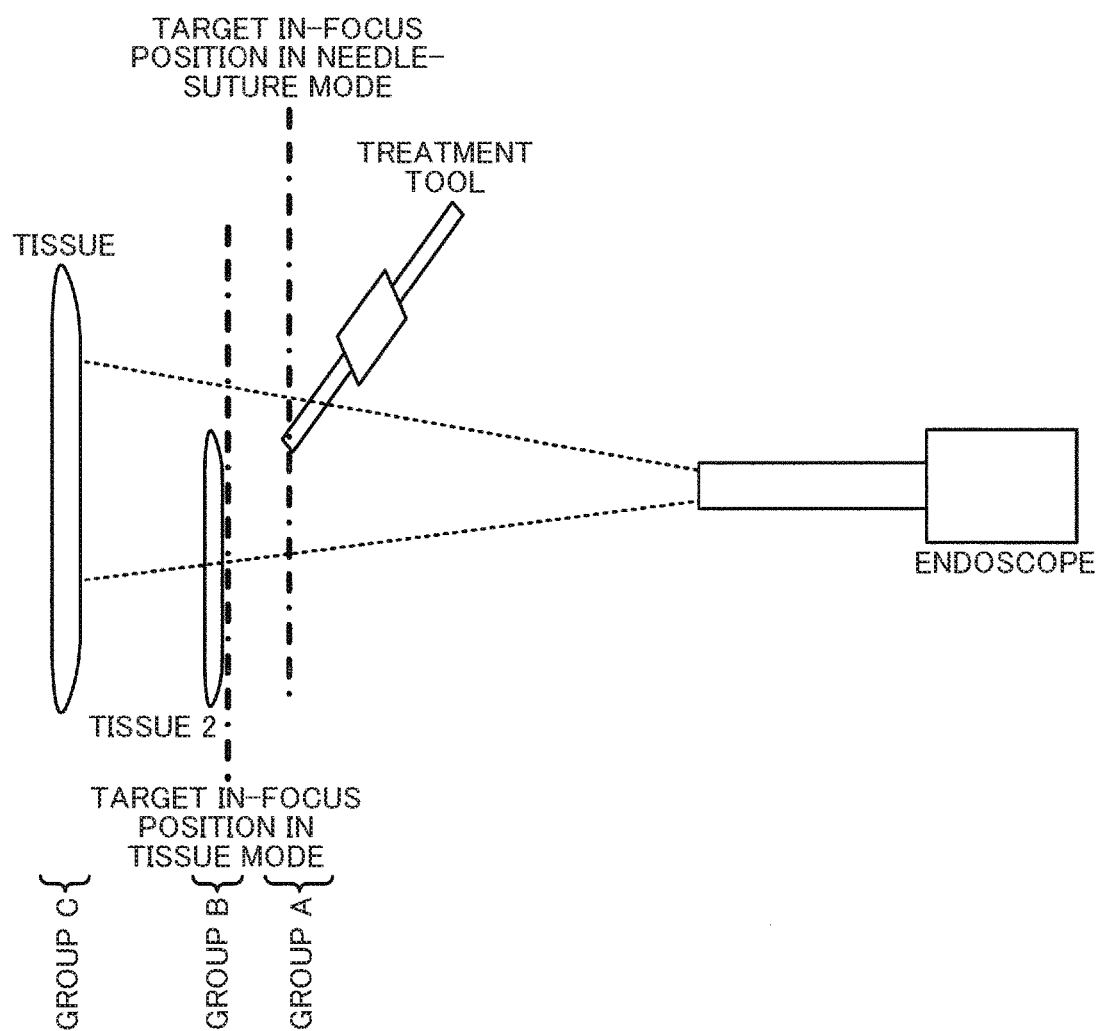
FIG. 11 is a view illustrating the relationship between the relative positional relationship between a plurality of objects and an imaging section, and a target in-focus position.
Figure 12A:
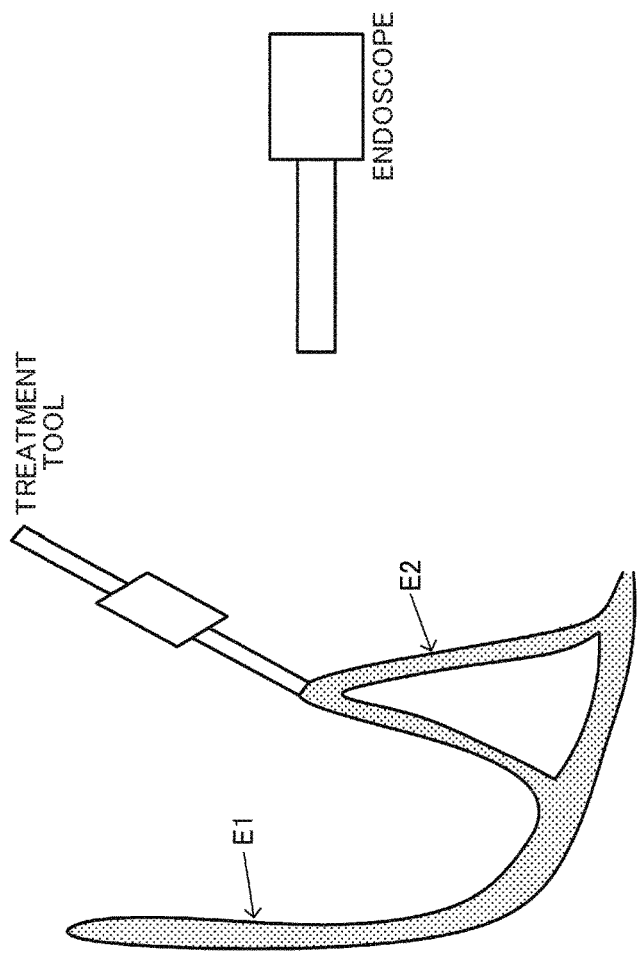
FIGS. 12A and 12B illustrate a specific example of a situation in which a plurality of tissues that differ in distance from an imaging section are captured.
Figure 12B:
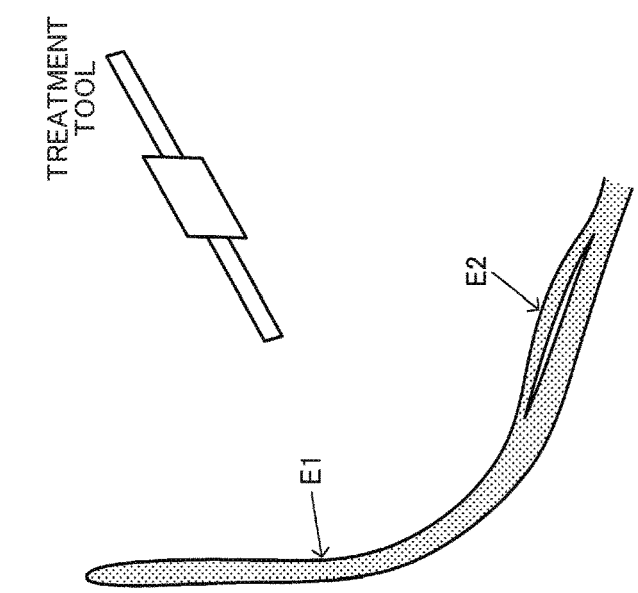

According to the above method, however, an appropriate result may not necessarily be obtained in the scene illustrated in FIG. 11. FIG. 11 illustrates an example of a scene that differs from the scene illustrated in FIG. 10. In the example illustrated in FIG. 11, a tissue 2 is added to the example illustrated in FIG. 10. The dotted lines indicate the range that can be captured within the AF area. Tissue, a treatment tool (e.g., forceps), and the tissue 2 are present within the range as objects. For example, FIG. 11 illustrates a scene in which membrane-like tissue E2 illustrated in FIG. 12A is pulled upward using forceps or the like (see FIG. 12B). Since tissue has a certain elasticity, tissue that differs from tissue that serves as a background is captured at a position closer to the endoscope in the same manner as in the example illustrated in FIG. 12B when tissue captured at the edge of the screen is moved toward the center of the image.

In the example illustrated in FIG. 11, the tissue 2 is situated so as to be captured more widely than the tissue. Therefore, it is desirable that the tissue 2 be brought into focus in the tissue mode, and the end of a treatment tool (e.g., forceps) that holds a needle and a suture be brought into focus in the needle-suture mode. When tissue is situated at two positions that differ in the depth direction, and the user is paying attention to the tissue that is situated on the rear side, it is considered that the position of the imaging section is adjusted so that the tissue that is situated on the front side does not lie within the AF area in which the main object is mainly captured, or does not occupy a large area within the AF area. For example, when the user is paying attention to the tissue indicated by E1 illustrated in FIG. 12A, the state illustrated in FIG. 12B does not occur since it is unnecessary to move the tissue indicated by E2 upward.

Specifically, when tissue that is situated on the front side occupies a large area within the AF area data (see FIG. 12B, for example), it is considered that the target in-focus position is the surface of tissue that is situated close to the endoscope.

When the comparative example is applied to the scene illustrated in FIG. 11, since an area (position) that is situated farthest from the image sensor 250 in terms of the object distance is brought into focus in the tissue mode, the tissue that is situated on the rear side may be brought into focus instead of the tissue 2. In one embodiment of the invention, the focus lens destination calculation process (S100) according to the comparative example illustrated in FIG. 7 is changed so that an appropriate AF process can be implemented even in the scene illustrated in FIG. 11. Note that the remaining process is the same as that of the comparative example, and description thereof is omitted.

Figure 13:
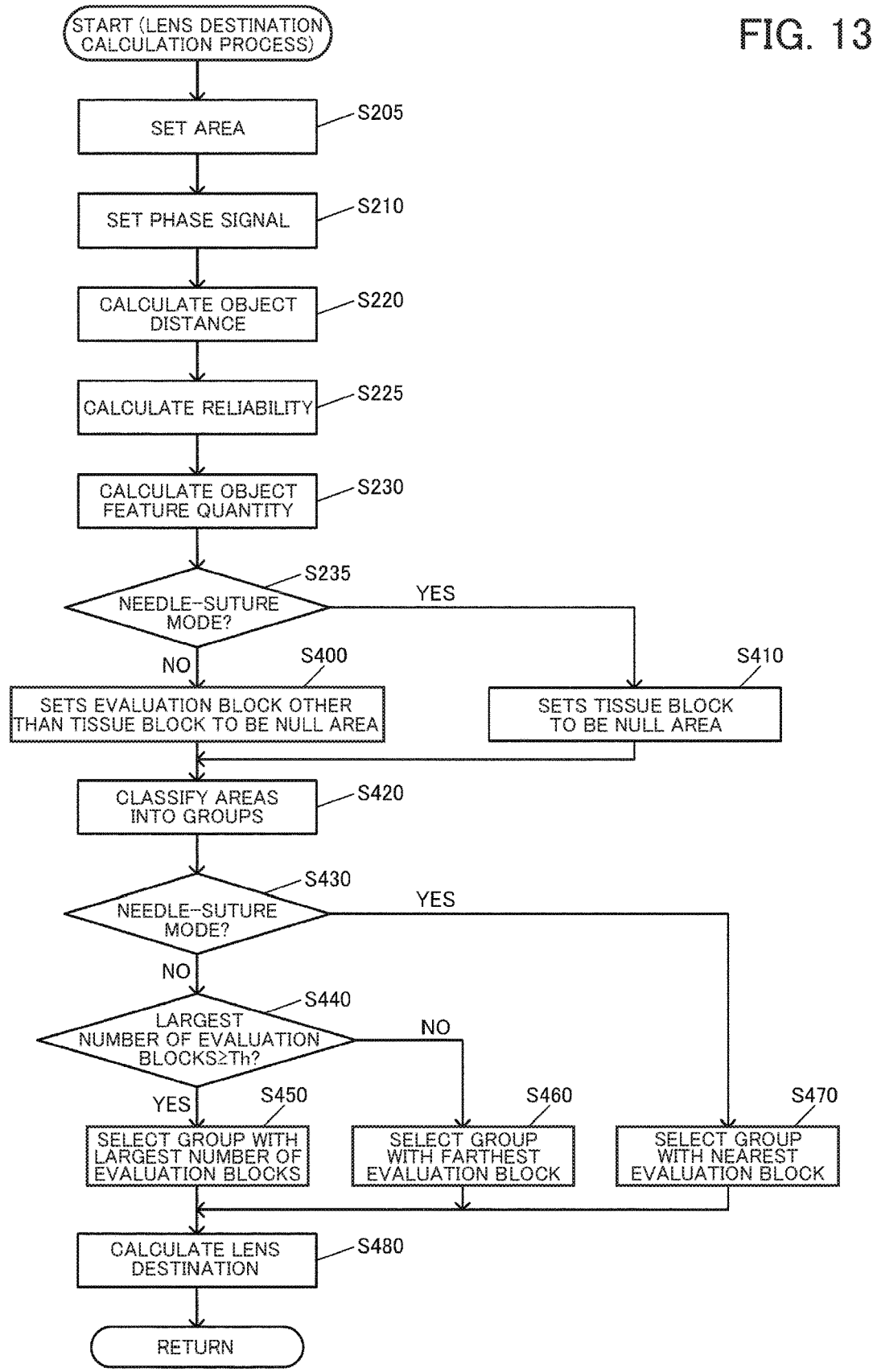
FIG. 13 is a flowchart illustrating a lens destination calculation process.

The details of the focus lens destination calculation process (S100) according to one embodiment of the invention are described below with reference to FIG. 13. Note that the same steps as those described above with reference to FIG. 7 are the same as described above, and description thereof is omitted.

In one embodiment of the invention, when the mode has been set to a mode other than the needle-suture mode, the area-of-interest estimation section 2070 determines the object captured within each evaluation block based on the object feature quantity with respect to each evaluation block, and determines whether or not each evaluation block is a tissue block in which only tissue is captured. The area-of-interest estimation section 2070 sets an evaluation block other than the tissue block to be a null block (S400). When all of the evaluation blocks are determined to be the null block, only evaluation blocks in a number equal to or less than a given number are set to be the null block (e.g., an evaluation block for which the object feature quantity represents a feature quantity close to that of tissue is not set to be the null block). This makes it possible to easily bring tissue into focus.

When the mode has been set to the needle-suture mode, the area-of-interest estimation section 2070 determines whether or not each evaluation block is the tissue block in the same manner as in the step S400. The area-of-interest estimation section 2070 sets the tissue block to be the null block (S410). When all of the evaluation blocks are determined to be the null block, only evaluation blocks in a number equal to or less than a given number are set to be the null block taking account of the ratio of tissue and the like. This makes it possible to easily bring an object (e.g., needle and suture) other than tissue into focus.

The area-of-interest estimation section 2070 classifies the evaluation blocks that have not been set to be the null block into two or more groups using at least the object distance (S420). For example, the evaluation blocks for which the object distance falls within a given range with respect to the evaluation block that is nearest to the image sensor 250 in terms of the object distance are classified as one group. The remaining evaluation blocks are classified into groups by repeating the above process. In this case, the evaluation blocks that are situated close to each other, and the evaluation blocks for which the object distance falls within a given range, may be classified as one group using the distance between the evaluation blocks within the image. The object distance with respect to each group is calculated. A value (e.g., mean value, median value, or mode) calculated based on a statistical method using the object distance with respect to each evaluation block that belongs to each group is taken as the object distance with respect to each group.

The area-of-interest estimation section 2070 then determines whether or not the mode set to the mode setting section 2020 is the needle-suture mode (S430). When the mode has been set to the needle-suture mode, a step S470 is performed. When the mode has been set to a mode other than the needle-suture mode, a step S440 is performed.

When the mode set to the mode setting section 2020 is not the needle-suture mode, the area-of-interest estimation section 2070 selects the group to which the largest number of evaluation blocks belong, and determines whether or not the number of evaluation blocks that belong to the selected group is equal to or larger than a given threshold value (S440). When the number of evaluation blocks that belong to the selected group is equal to or larger than the given threshold value, a step S450 is performed. When the number of evaluation blocks that belong to the selected group is smaller than the given threshold value, a step S460 is performed. Although an example in which the number of evaluation blocks that belong to the selected group is compared with the given threshold value has been described above, the ratio of the number of evaluation blocks that belong to the selected group to the total number of evaluation blocks may also be used. Although an example in which the determination process is performed in the step S440 using the number of evaluation blocks and the given threshold value has been described above, the determination process may be performed using the total area of the evaluation blocks that belong to the selected group, the ratio of the total area of the evaluation blocks that belong to the selected group with respect to the AF area, the ratio of the total area of the evaluation blocks that belong to the selected group with respect to the entire image, or the like.

When the number of evaluation blocks that belong to the selected group is equal to or larger than the given threshold value, the area-of-interest estimation section 2070 selects the group to which the largest number of evaluation blocks belong (S450). When the number of evaluation blocks that belong to the selected group is smaller than the given threshold value, the area-of-interest estimation section 2070 selects the group to which the evaluation block that is farthest from the image sensor 250 in terms of the object distance belongs (S460). In the step S460, the group that is farthest from the image sensor 250 in terms of the object distance calculated in the step S420 may be selected. Since the object distance with respect to each group is calculated using a statistical method, it is possible to reduce or suppress the effect of noise due to the image sensor 250, and disturbance due to a treatment tool and the like.

When the mode has been set to the needle-suture mode, the area-of-interest estimation section 2070 selects the group to which the evaluation block that is nearest to the image sensor 250 in terms of the object distance belongs (S470). In the step S470, the group that is nearest to the image sensor 250 in terms of the object distance calculated in the step S420 may be selected. Since the object distance with respect to each group is calculated using a statistical method, it is possible to reduce or suppress the effect of noise due to the image sensor 250, and disturbance due to a treatment tool and the like.

The area-of-interest estimation section 2070 calculates the average object distance with respect to each evaluation block that belongs to the group selected in the step S450, S460, or S470, and determines the lens position at which the object is brought into focus at the average object distance to be the lens destination (S480). In this case, a lens position at which the object is brought into focus at an offset object distance may be determined to be the lens destination corresponding to the mode, the distribution of the object distance with respect to each evaluation block, the distribution of the object feature quantity, and the like. The average object distance is not limited to the average object distance with respect to each evaluation block that belongs to the selected group. Another value (e.g., median value, mode, maximum value, or minimum value) based on a statistical method may also be used.

When one embodiment of the invention is applied to the scene illustrated in FIG. 11, the evaluation blocks are classified into the group A, the group B, and the group C illustrated in FIG. 11 (step S420) since the evaluation block in which the treatment tool is captured, the evaluation block in which the tissue 2 is captured, and the evaluation block in which the tissue is captured, differ from each other as to the object distance. When the null block is used, the group A may not be set since the evaluation block in which the treatment tool is captured is set to the null block in the tissue mode. However, an evaluation block in which tissue and a treatment tool are captured may not be set to the null block, and the null block may not be set since the steps S400 to S420 are not indispensable. Therefore, the following description is given on the assumption that the group A that corresponds to the treatment tool is set even in the tissue mode.

In the needle-suture mode, the group A to which the evaluation block that is nearest to the image sensor 250 in terms of the object distance belongs, is selected in the step S470. This makes it possible to implement an appropriate AF process when the user manipulates a needle and a suture.

In the tissue mode, the group B to which the largest number of evaluation blocks belong is selected in the step S450 by appropriately setting the given threshold value Th used in the step S440. This makes it possible to bring the tissue 2 that is considered to be of interest to the user into focus.

When the tissue 2 (see FIG. 11) is captured to only a small extent, the group C to which the evaluation block that is farthest from the image sensor 250 in terms of the object distance belongs, is selected in the step S460. This makes it possible to bring the tissue that is considered to be of interest to the user into focus. Specifically, it is possible to bring the tissue 2 situated close to the image sensor 250 into focus, or bring the tissue situated away from the image sensor 250 into focus, corresponding to the number of evaluation blocks that belongs to each group.

According to the embodiments of the invention, an area that is of interest to the user of an endoscope (i.e., an area to which the user of an endoscope is paying attention) is estimated using the object distance with respect to each of a plurality of evaluation areas, and the focus lens is driven based on the estimation result. This makes it possible to bring the object of interest into focus without requiring the user to perform a complex operation. When the mode has been set to the needle-suture mode, it is possible to bring the object of interest into focus while preventing a situation in which tissue is necessarily brought into focus, by changing the evaluation block setting method, and estimating an area that is of interest to the user in a different way. It is possible to bring an appropriate tissue into focus without requiring the user to perform an operation even in a scene in which a plurality of tissues are situated at different positions in the optical axis direction (see FIG. 11), by performing the classification process, and performing the process that uses the area information about each group.

4. Specific Example

According to the embodiments of the invention, when it has been determined that the area of a largest area group that is a group among the plurality of groups that has the largest area is equal to or larger than a given threshold value based on the area information, the focus control section 2095 performs the focus control process that brings the largest area group into focus.

More specifically, the area information is calculated with respect to each of the plurality of groups, and a group among the plurality of groups for which the area represented by the area information is largest, is determined to be the largest area group. In the example illustrated in FIG. 11, the area $S_A$ of the group A, the area $S_B$ of the group B, and the area $S_C$ of the group C are calculated, and compared with each other.

This makes it possible to determine the largest area group that has the largest area, and determine the magnitude of the area of the largest area group. This control process is performed in the tissue mode in a narrow sense (see the step S440 in FIG. 13). In this case, the largest area group is brought into focus on condition that the area of the largest area group is equal to or larger than a given threshold value. When a group that occupies a large area within the captured image is not present (e.g., when a number of groups having a relatively small area have been set), the user is not necessarily paying attention to the largest area group even if a given group has been determined to be the largest area group. Specifically, when the user is paying attention to a specific object (tissue), it is considered that the imaging section 200 is operated so that the object becomes dominant within the captured image. Since the area comparison process using a given standard (i.e., threshold value) is also performed instead of merely comparing the groups as to the area, it is possible to improve the object-of-interest determination accuracy. Note that another information that represents an area (e.g., the number of evaluation blocks that belong to each group, or the ratio of the number of evaluation blocks that belong to each group) may also be used as the area information (see above). Specifically, the determination process that determines whether or not the area of the group is equal to or larger than a given threshold value may be implemented by a determination process that determines whether or not the number of evaluation blocks is equal to or larger than a given threshold value, for example.

When it has been determined that the area of the largest area group is smaller than the given threshold value, the focus control section 2095 may perform the focus control process that brings a group among the plurality of groups that is farthest in terms of the distance represented by the distance information, into focus.

This makes it possible to bring the group that is situated away from the imaging section 200 into focus when the largest area group does not occupy a large area within the captured image (i.e., when it is difficult to determine that a specific group corresponds to the object of interest based on the area information). This process is a control process that preferentially bring an object situated away from the imaging section 200 into focus. The advantage of this control process has been described above.

In this case, the focus control section 2095 may determine the group that is farthest in terms of the distance represented by the distance information based on the distance information about each of the plurality of areas classified into the plurality of groups. For example, an area among the plurality of areas that is farthest in terms of the distance represented by the distance information may be determined, and the group that includes the determined area may be determined to be the group that is farthest in terms of the distance represented by the distance information. Alternatively, the distance with respect to each group may be calculated based on the distance information about each area classified into the plurality of groups. For example, a value (e.g., mean value, median value, or mode) calculated based on a statistical method using the object distance with respect to each area that belongs to each group may be taken as the object distance with respect to each group (see above). When the distance with respect to each group has been calculated, the group having the maximum distance is determined to be the group that is farthest in terms of the distance represented by the distance information.

Note that both the control process performed when it has been determined that the area of the largest area group is equal to or larger than the given threshold value, and the control process performed when it has been determined that the area of the largest area group is smaller than the given threshold value, need not necessarily performed. Only one of these control processes may be performed.

The focus control section 2095 may have a first mode in which the focus control section performs the focus control process that preferentially brings a group among the plurality of groups that is farthest in terms of the distance represented by the distance information, into focus, and a second mode in which the focus control section performs the focus control process that preferentially brings a group among the plurality of groups that is nearest in terms of the distance represented by the distance information, into focus.

Figure 2:
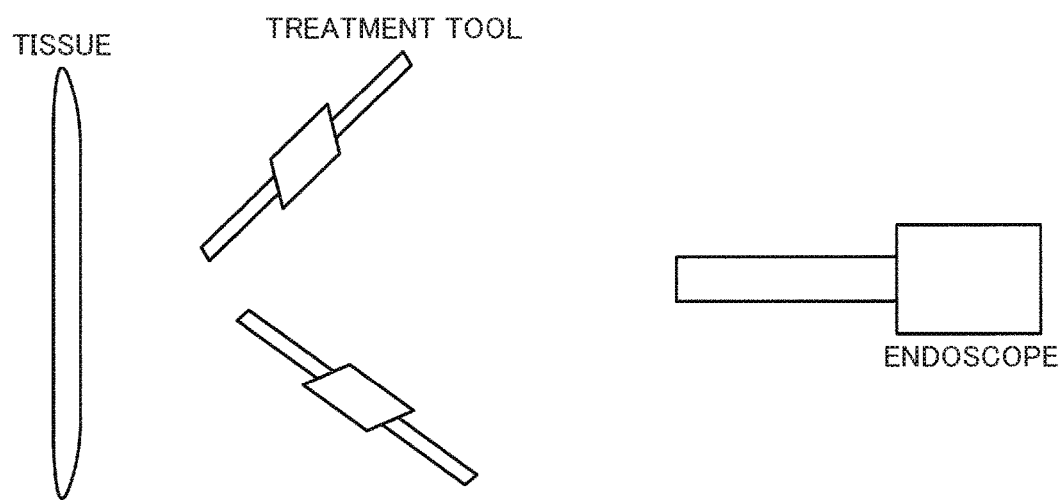
FIG. 2 illustrates an example of the positional relationship between an endoscope apparatus (imaging section) and a plurality of objects.

The first mode is the tissue mode in a narrow sense, and the second mode is the needle-suture mode (treatment tool mode) in a narrow sense. This makes it possible to implement the focus control process based on the area information, and flexibly change the focus control process. In the tissue mode, it is unlikely that an object that is not of interest to the user lies behind the object of interest to the user (see above). Therefore, it is effective to preferentially bring the object situated away from the imaging section 200 into focus. However, when the object of interest is not tissue, the object of interest may not be brought into focus when the object situated away from the imaging section 200 is preferentially brought into focus. For example, it is considered that a treatment tool (e.g., forceps) is captured in front of tissue (see FIG. 2). Therefore, if the object situated away from the imaging section 200 is preferentially brought into focus, tissue that lies behind the treatment tool is brought into focus even when the user is paying attention to the treatment tool. Since the treatment tool has a thin rod-like shape or the like, the treatment tool does not necessarily occupy a very large area within the captured image even when the user is paying attention to the treatment tool, for example, and the treatment tool may not be appropriately brought into focus even when an object for which the area represented by the area information is large is preferentially brought into focus. It is possible to deal with various situations by switching the focus control process corresponding to the mode.

The focus control section 2095 may calculate the feature quantity with respect to each of the plurality of areas, and may set a null area based on the feature quantity, the null area being an area that is not subjected to the classification process.

This makes it possible to implement a process that uses the feature quantity with respect to each area. More specifically, the object captured within each area may be determined from the feature quantity. In this case, it is possible to determine whether or not the object of interest is captured within each area by utilizing the feature quantity. It is possible to prevent a situation in which an inappropriate area is brought into focus by setting an area in which the object of interest is not captured to be the null area (null block) that is not subjected to the subsequent process.

Specifically, the focus control section 2095 may set an area among the plurality of areas for which it has been determined that an object other than tissue is captured, to be the null area based on the feature quantity. More specifically, the focus control section 2095 may set an area for which it has been determined that an object other than tissue is captured, to be the null area in the first mode, and may set an area for which it has been determined that tissue is captured, to be the null area in the second mode.

This makes it possible to set an appropriate area to be the null area corresponding to the mode. Specifically, it is possible to prevent a situation in which an object other than tissue is brought into focus in the tissue mode by setting an object other than tissue to be the null area, and prevent a situation in which tissue is brought into focus in a mode (needle-suture mode in a narrow sense) other than the tissue mode by setting tissue to be the null area. FIGS. 14A and 14B illustrate a specific example of the null area and the effective area. As illustrated in FIG. 14A, since tissue is the object of interest in the tissue mode, the blocks in which the treatment tool is captured are set to "NULL". As illustrated in FIG. 14B, since an area around the end of forceps that hold a needle and a suture is the object of interest in the needle-suture mode, the blocks in which tissue is captured are set to "NULL".

Although an example in which the null area is used has been described above, an effective area may be set, and the classification process may be performed on the effective area. More specifically, the focus control section 2095 may calculate the feature quantity with respect to each of the plurality of areas, and may set an area among the plurality of areas to be an effective area that is subjected to the classification process based on the feature quantity.

This also makes it possible to prevent a situation in which an inappropriate area is brought into focus since an area in which the object of interest is captured is selected, and subjected to the subsequent process.

Specifically, the focus control section 2095 may set an area among the plurality of areas for which it has been determined that tissue is captured, to be the effective area based on the feature quantity. More specifically, the focus control section 2095 may set an area for which it has been determined that tissue is captured, to be the effective area in the first mode, and may set an area for which it has been determined that an object other than tissue is captured, to be the effective area in the second mode.

The focus control section 2095 may switch the mode between the first mode and the second mode based on an operation performed by the user.

This makes it possible to switch the mode based on an operation performed by the user. Note that the operation performed by the user is performed using an operation section, for example. The operation section may be provided to the imaging section 200, or may be implemented by the external I/F section 500. The mode may be switched using another method. For example, the mode may be automatically switched by the focus control device.

The focus control section 2095 may perform the focus control process in the first mode using a first threshold value as the given threshold value, and may perform the focus control process in the second mode using a second threshold value that differs from the first threshold value as the given threshold value.

The given threshold value is the threshold value used for the comparison process with respect to the largest area group. The first feature of the above configuration is that the control process that uses the area information may also be performed in the second mode. More specifically, a comparison process that compares the area information about the largest area group with the given threshold value is performed. The second feature of the above configuration is that a different threshold value is used in the first mode and the second mode when performing the comparison process.

In the second mode, the object of interest is a treatment tool (e.g., forceps) (i.e., a needle and a suture held by the end of the treatment tool in a narrow sense). However, it is unlikely that the treatment tool (e.g., needle and suture) is captured to occupy a large area within the captured image taking account of the size, the shape, and the like. Specifically, the given threshold value used in the first mode is set to be a value (e.g., 50 to 70%) sufficient to determine that the user is paying attention to the group. However, such a value is not appropriately as the given threshold value used in the second mode. Therefore, the given threshold value used in the second mode should be milder than the given threshold value used in the first mode in terms of a condition. More specifically, the given threshold value used in the second mode is set so that the value represented by the area information exceeds the threshold value even when the area of the largest area group is not sufficiently large.

The process that is performed in the second mode using the area information aims to improve the object-of-interest determination accuracy, for example. It is considered that the object of interest is situated close to the imaging section 200 in the needle-suture mode, and the object of interest can be brought into focus even if the focus control process is performed without using the area information (see the steps S430 and S470 in FIG. 13 (flowchart)). However, if a determination error has occurred in the distance information calculation process or the like, the group that is situated close to the imaging section 200 may be set although such an object does not exist. Since it is unlikely that such a determination error occurs over a number of areas (evaluation blocks), it is considered that the group set due to a determination error does not have a large area. Specifically, it is possible to reduce the possibility that the an erroneous determination result affects the focus control process, and implement an accurate focus control process by performing the focus control process that brings a group that is situated close to the imaging section 200 and has an area equal to or larger than a given area, into focus. For example, the given threshold value used in the second mode may be set to a value that is sufficiently large so that the effect of a determination error due to noise or the like can be reduced or suppressed, and is smaller than the value used in the first mode (i.e., a value determined from the ratio of forceps with respect to the captured image).

Note that the method that uses the area information in the second mode is not limited to the above method. Various modifications and variations may be made. For example, when a plurality of groups that are situated closer to the imaging section 200 than a given reference position have been detected, a group among the plurality of groups that has the largest area may be brought into focus.

The area setting section 2010 may change at least one of the positions, the size, and the number of the areas to be set to the captured image when the focus control section 2095 has set the mode to the second mode as compared with a case where the focus control section 2095 has set the mode to the first mode.

This makes it possible to set an appropriate area to be the null area corresponding to the mode (i.e., corresponding to the object of interest in each mode in a narrow sense). In the second mode illustrated in FIG. 8B, the size of the areas (evaluation blocks) is small, and the number of areas (evaluation blocks) is large as compared with the first mode illustrated in FIG. 8A. This is because the object of interest (i.e., needle and suture) in the second mode is small and thin as compared with the object of interest (i.e., tissue) in the first mode. The AF area may be set to a lower part of the image in the second mode as compared with the first mode (see above). In this case, the positions of the evaluation blocks also change.

The object distance information calculation section 2040 may calculate the reliability that represents the probability that the distance information calculated with respect to each of the plurality of areas is reliable.

This makes it possible to determine whether or not the distance information is reliable. In this case, the focus control section 2095 may set a null area based on the reliability, the null area being an area that is not subjected to the classification process. According to this configuration, when the distance information with respect to a given area is not reliable, the given area can be excluded from the processing target, and it is possible to prevent a situation in which an inappropriate direction is determined to be the focus target. Specifically, the null area may be set using the feature quantity, or may be set using the reliability, or may be set using both the feature quantity and the reliability.

The object distance information calculation section 2040 may acquire phase difference information from a phase sensor with respect to each of the plurality of areas, and may calculate the distance information based on the phase difference information.

The phase sensor is the phase sensors S1 and S2 illustrated in FIG. 4, for example. The phase difference information is information obtained by performing a comparison process on the signal from the phase sensor S1 and the signal from the phase sensor S2. In this case, the area setting section 2010 may set the plurality of areas based on the placement information about the phase sensor (S1, S2) in the imaging section 200.

When the phase difference signal is used to calculate the distance information, an area that is used as the distance information calculation unit must include at least one phase sensor S1 and at least one phase sensor S2 that output information from which the phase difference information can be calculated. If an area that corresponds to a given evaluation block does not include at least one of the phase sensors S1 and S2, it is impossible to calculate the phase difference signal and the distance information with respect to the given evaluation block.

However, a mode that replaces the phase sensors (i.e., image sensor 250) of the imaging section 200 is not common, and the arrangement pattern of the phase sensors is limited even if the phase sensors can be replaced. Specifically, the arrangement of the phase sensors is determined in terms of hardware, it is difficult to change the arrangement of the phase sensors later. Therefore, it is considered that it is realistic to determine the arrangement pattern of the phase sensors, and set areas corresponding to the arrangement pattern of the phase sensors in order to ensure that the areas (evaluation blocks) used as the distance information calculation unit and the phase sensors have an appropriate relationship.

Note that it suffices that it is possible to acquire the object distance with respect to each evaluation block, and a sensor other than a phase sensor may also be used. For example, the object distance information calculation section 2040 may calculate the distance information based on the captured image acquired by applying given patterned light. Specifically, light having a specific pattern is applied to the object. The reflected light is acquired, and a change in shape of the pattern is analyzed to acquire the distance to the object. The object distance can be calculated from the distance to the object and the characteristics of the lens.

Alternatively, a method widely used for an active AF process may be used. More specifically, the imaging section 200 may include a range sensor (not illustrated in FIG. 3 and the like), and the object distance information calculation section 2040 may calculate the distance information based on sensor information from the range sensor. The range sensor may be configured in various ways. For example, the range sensor may apply light such as infrared light to the object, and receive the reflected light from the object. In this case, the distance to the object can be calculated based on the time from the irradiation timing to the reflected light reception timing.

The object distance information calculation section 2040 may calculate the distance information based on the AF evaluation value (contrast value) calculated from the captured image. The AF evaluation value is information that is used for a contrast AF process. For example, an arbitrary bad-pass filter (BPF) process may be performed on the Y signal and the G signal of each pixel included in the processing target area, and the sum of the output values may be used as the AF evaluation value. Various calculation methods are known with regard to the AF evaluation value used for the contrast AF process. Various methods other than the BPF process can be widely applied to the embodiments of the invention.

When the AF evaluation value is used, the object distance information calculation section 2040 calculates the AF evaluation with respect to each evaluation block (processing target area) while changing the in-focus object plane position, and calculates the peak position of the AF evaluation value on an evaluation block basis. More specifically, the in-focus object plane position is changed over a certain range by controlling the focus lens 220. It suffices that the range in which the in-focus object plane position is changed be a range that is considered to include the in-focus object plane position at which the AF evaluation value peaks. The range in which the in-focus object plane position is changed may be the entire range of the in-focus object plane position determined based on the configuration of the imaging section 200 in a narrow sense. The focus lens 220 may be controlled to move from the WIDE end (TELE end) to the TELE end (WIDE end). Note that the focus lens 220 may be controlled in another way as long as the in-focus object plane position is changed to cover the above range.

The peak position of the AF evaluation value within the range in which the in-focus object plane position is changed is thus calculated with respect to each evaluation block. As is known as a common contrast AF method, when the contrast value calculated from a given area has peaked at a given in-focus object plane position, it is considered that the object captured within the given area is brought into focus by setting the in-focus object plane position to the given position (i.e., the object lies at the in-focus object plane position). Specifically, when the peak position has been determined, it is determined that the distance to the object captured within the processing target evaluation block corresponds to the distance to the in-focus object plane position. When the position of the focus lens 220 is controlled, the position of the focus lens 220 at which the AF evaluation value peaks is calculated directly. However, since the relationship between the position of the focus lens 220 and the in-focus object plane position can be determined in advance, it is easy to converting the position of the focus lens 220 into the in-focus object plane position.

The distance information with respect to each evaluation block can be acquired by performing the above process. After the distance information with respect to each evaluation block has been acquired, the subsequent process is performed in the same manner as described above in connection with the method that utilizes the phase sensor or the like.

The embodiments of the invention are not limited to the focus control device, and may also be applied to an endoscope apparatus (endoscope system) that includes the focus control device. Specifically, the embodiments of the invention may be applied to the endoscope system illustrated in FIG. 3. In this case, the captured image is an in vivo image, and it is possible to implement an endoscope apparatus that can preferentially bring tissue that is situated away from the imaging section 200 into focus, and can optionally bring tissue that is situated on the front side, a treatment tool, or the like into focus, while performing the focus control process based on the area information.

Each process performed by the image processing device according to the embodiments described above (i.e., each process illustrated in each flowchart) may be stored in the form of a program that can be executed by the control section 350. The program may be stored in a storage device (storage medium) of an external storage device such as a memory card (e.g., ROM card and RAM card), a magnetic disk (e.g., floppy disk and hard disk), an optical disk (e.g., CD-ROM and DVD), or a semiconductor memory, and distributed. The control section 350 may read the program stored in the storage device of the external storage device, and may be controlled by the program to implement the above process.

The focus control device and the like according to the embodiments of the invention may include a processor and a memory. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an application-specific integrated circuit (ASIC). The memory stores a computer-readable instruction. Each section of the focus control device and the like according to the embodiments of the invention is implemented by causing the processor to execute the instruction. The memory may be a semiconductor memory (e.g., SRAM or DRAM), a register, a hard disk, or the like. The instruction may be an instruction included in an instruction set that is included in a program, or may be an instruction that causes a hardware circuit included in the processor to operate.

5. Modification

Mist (e.g., water vapor and minute particles) is produced when the user excises tissue using an energy device or the like, for example. When mist has been produced, light emitted from the white light source 610 (light emitted from the light guide section 120) may be diffusely reflected, and it may be impossible to accurately estimate the object distance. Since mist is an object that changes to a large extent with the passing of time, the object distance calculated by the object distance calculation process (step S220 in FIG. 13) and the reliability calculated by the reliability calculation process (step S230 in FIG. 13) may change to a large extent each time the object distance or the reliability is calculated.

Figure 15:
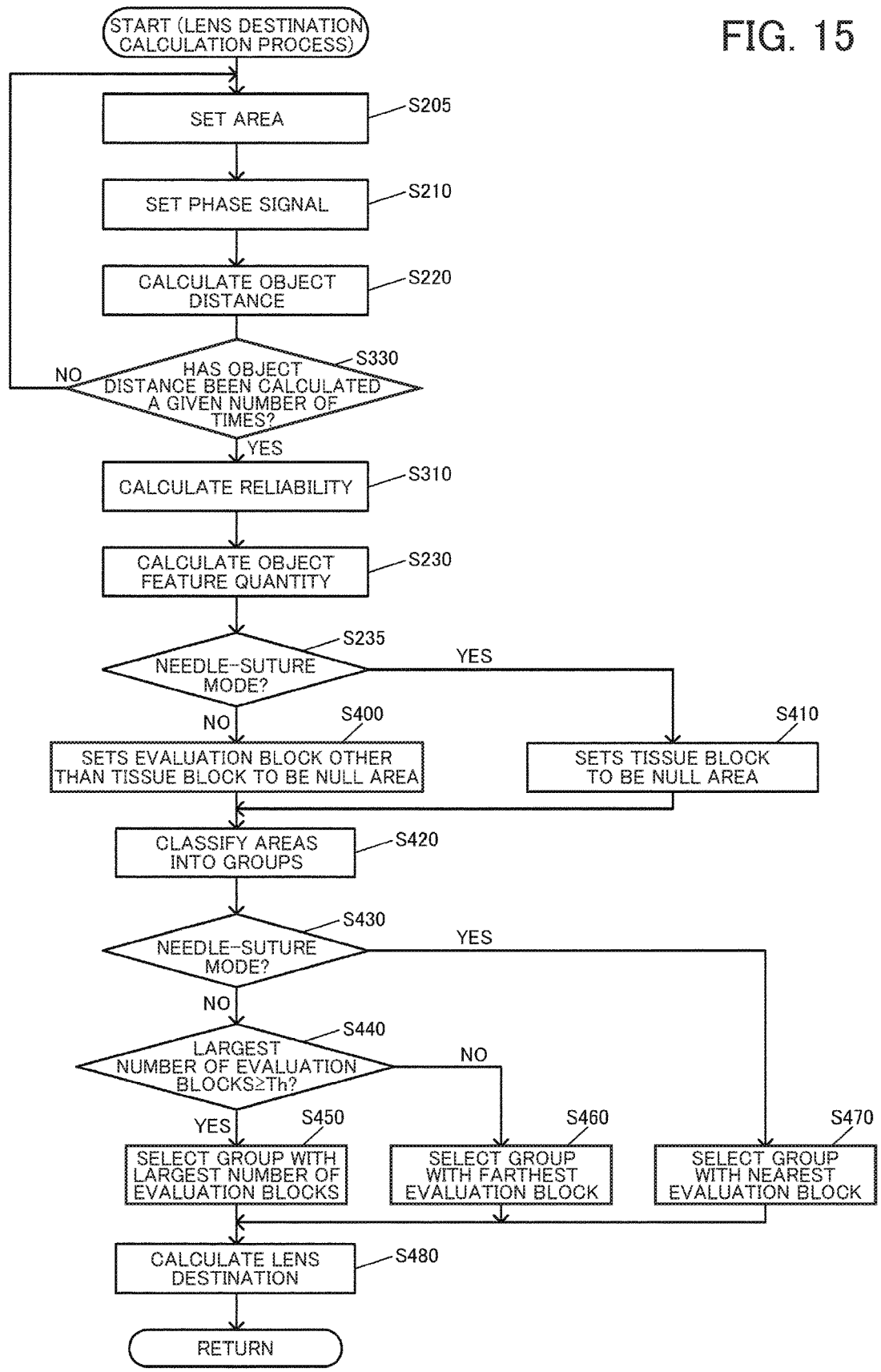
FIG. 15 is a flowchart illustrating a lens destination calculation process.

Therefore, when the object changes to a large extent (e.g., due to production of mist), the reliability is decreased when the object distance changes to a large extent with the passing of time. The focus lens destination calculation process (S100) according to the modification is illustrated in FIG. 15. Note that the same steps as those described above with reference to FIG. 13 are the same as described above, and description thereof is omitted.

When the steps S200 to S220 have been performed, the reliability calculation section 2050 determines whether or not the object distance has been calculated a given number of times (S300). When the object distance has been calculated a given number of times (e.g., five times), a step S310 is performed. When the object distance has not been calculated a given number of times, the steps S205 to S220 are performed on another image output from the A/D conversion section 310 (i.e., an image captured at a different timing). Note that whether or not the object distance has been calculated a plurality of times within a given error range may be determined instead of determining whether or not the object distance has been calculated a given number of times, for example.

The reliability calculation section 2050 calculates the reliability based on the degree of dispersion of the object distances calculated a plurality of times (S310). The reliability may be calculated using the degree of dispersion of the object distances calculated a plurality of times, and the degree of correlation when the phase difference is calculated by the object distance information calculation section 2040.

Note that the object distance with respect to each evaluation block used in the subsequent steps is the object distance calculated first, the object distance calculated last, a statistically calculated value (e.g., mean value, median value, mode, maximum value, or minimum value) of the object distances calculated a plurality of times, or the like.

According to the modification, it is possible to calculate more accurate reliability in a scene in which the object changes to a large extent (e.g., when mist has been produced) while achieving the advantageous effects according to the embodiments of the invention. This makes it possible to reduce or suppress a situation in which an object (position) that is not intended by the user is brought into focus, and implement a stable AF process.

Although only some embodiments of the present invention and the modifications thereof have been described in detail above, those skilled in the art will readily appreciate that many modifications are possible in the embodiments without materially departing from the novel teachings and advantages of the invention. Accordingly, all such modifications are intended to be included within scope of the invention. Any term cited with a different term having a broader meaning or the same meaning at least once in the specification and the drawings can be replaced by the different term in any place in the specification and the drawings. The configurations and the operations of the focus control device and the endoscope apparatus are not limited to those described above in connection with the embodiments. Various modifications and variations may be made of those described above in connection with the embodiments.

What is claimed is:

1. A focus control device comprising:
 a processor comprising hardware, the processor being configured to implement:
 a region setting process that sets a plurality of regions to a captured image that has been captured by an image sensor, each of the plurality of regions including a plurality of pixels;
 an object distance information calculation process that calculates distance information about a distance to an object that is captured within each of the plurality of regions; and
 a focus control process based on the distance information,
 wherein the processor implements the focus control process that performs a classification process that classifies the plurality of regions into a plurality of groups based on the distance information,
 wherein, when it has been determined based on area information about each of the plurality of groups that an area of a largest area group, which is a group from among the plurality of groups that has a largest area, is equal to or larger than a given threshold value, the processor implements the focus control process that brings the largest area group into focus based on the area information about each of the plurality of groups.

2. The focus control device as defined in claim 1, wherein, when it has been determined that the area of the largest area group is smaller than the given threshold value, the processor implements the focus control process that brings a group among the plurality of groups that is farthest in terms of the distance represented by the distance information, into focus.

3. The focus control device as defined in claim 2, wherein the processor implements the focus control process that determines the group that is farthest in terms of the distance represented by the distance information based on the distance information about each of the plurality of regions classified into the plurality of groups.

4. A focus control device comprising:
 a processor comprising hardware, the processor being configured to implement:
 a region setting process that sets a plurality of regions to a captured image that has been captured by an image sensor, each of the plurality of regions including a plurality of pixels;
 an object distance information calculation process that calculates distance information about a distance to an object that is captured within each of the plurality of regions; and
 a focus control process based on the distance information,
 wherein the processor implements the focus control process that performs a classification process that classifies the plurality of regions into a plurality of groups based on the distance information, and
 wherein, when it has been determined based on area information about each of the plurality of groups that an area of a largest area group, which is a group among the plurality of groups that has a largest area, is smaller than the given threshold value, the processor implements the focus control process that brings a group among the plurality of groups that is farthest in terms of the distance represented by the distance information, into focus, based on the area information about each of the plurality of groups.

5. A focus control device comprising:
a processor comprising hardware, the processor being configured to implement:
a region setting process that sets a plurality of regions to a captured image that has been captured by an image sensor, each of the plurality of regions including a plurality of pixels;
an object distance information calculation process that calculates distance information about a distance to an object that is captured within each of the plurality of regions; and
a focus control process based on the distance information,
wherein the processor implements the focus control process that performs a classification process that classifies the plurality of regions into a plurality of groups based on the distance information, and brings a group among the plurality of groups into focus, the group that is brought into focus having an area which has been determined to be equal to or larger than a given threshold value based on area information about each of the plurality of groups, and
wherein the processor implements the focus control process that has a first mode in which the processor implements the focus control process that preferentially brings a group among the plurality of groups that is farthest in terms of the distance represented by the distance information, into focus, and a second mode in which the processor implements the focus control process that preferentially brings a group among the plurality of groups that is nearest in terms of the distance represented by the distance information, into focus.

6. A focus control device comprising:
a processor comprising hardware, the processor being configured to implement:
a region setting process that sets a plurality of regions to a captured image that has been captured by an image sensor, each of the plurality of regions including a plurality of pixels;
an object distance information calculation process that calculates distance information about a distance to an object that is captured within each of the plurality of regions; and
a focus control process based on the distance information,
wherein the processor implements the focus control process that performs a classification process that classifies the plurality of regions into a plurality of groups based on the distance information, and brings a group among the plurality of groups into focus, the group that is brought into focus having an area which has been determined to be equal to or larger than a given threshold value based on area information about each of the plurality of groups, and
wherein the processor implements the focus control process that calculates a feature quantity with respect to each of the plurality of regions, and sets a null region based on the feature quantity, the null region being a region that is not subjected to the classification process.

7. The focus control device as defined in claim 6, wherein the processor implements the focus control process that sets a region among the plurality of regions for which it has been determined that an object other than tissue is captured, to be the null region based on the feature quantity.

8. The focus control device as defined in claim 6, wherein:
the processor implements the focus control process that has a first mode in which the processor implements the focus control process that preferentially brings a group among the plurality of groups that is farthest in terms of the distance represented by the distance information, into focus, and a second mode in which the processor implements the focus control process that preferentially brings a group among the plurality of groups that is nearest in terms of the distance represented by the distance information, into focus, and
the processor implements the focus control process that sets a region among the plurality of regions for which it has been determined that an object other than tissue is captured, to be the null region in the first mode, and sets an region among the plurality of regions for which it has been determined that the tissue is captured, to be the null region in the second mode.

9. A focus control device comprising:
a processor comprising hardware, the processor being configured to implement:
a region setting process that sets a plurality of regions to a captured image that has been captured by an image sensor, each of the plurality of regions including a plurality of pixels;
an object distance information calculation process that calculates distance information about a distance to an object that is captured within each of the plurality of regions; and
a focus control process based on the distance information,
wherein the processor implements the focus control process that performs a classification process that classifies the plurality of regions into a plurality of groups based on the distance information, and brings a group among the plurality of groups into focus, the group that is brought into focus having an area which has been determined to be equal to or larger than a given threshold value based on area information about each of the plurality of groups, and
wherein the processor implements the focus control process that calculates a feature quantity with respect to each of the plurality of regions, and sets an effective region based on the feature quantity, the effective region being a region among the plurality of regions that is subjected to the classification process.

10. The focus control device as defined in claim 9, wherein the processor implements the focus control process that sets a region among the plurality of regions for which it has been determined that tissue is captured, to be the effective region based on the feature quantity.

11. The focus control device as defined in claim 9, wherein:
the processor implements the focus control process that has a first mode in which the processor implements the focus control process that preferentially brings a group among the plurality of groups that is farthest in terms of the distance represented by the distance information, into focus, and a second mode in which the processor implements the focus control process that preferentially brings a group among the plurality of groups that is nearest in terms of the distance represented by the distance information, into focus, and
the processor implements the focus control process that sets a region among the plurality of regions for which it has been determined that tissue is captured, to be the effective region in the first mode, and sets a region among the plurality of regions for which it has been determined that an object other than the tissue is captured, to be the effective region in the second mode.

12. The focus control device as defined in claim 5, wherein the processor implements the focus control process that switches a mode between the first mode and the second mode based on an operation performed by a user.

13. The focus control device as defined in claim 1, wherein:
the processor implements the focus control process that has a first mode in which the processor implements the focus control process that preferentially brings a group among the plurality of groups that is farthest in terms of the distance represented by the distance information, into focus, and a second mode in which the processor implements the focus control process that preferentially brings a group among the plurality of groups that is nearest in terms of the distance represented by the distance information, into focus, and
the processor implements the focus control process in the first mode using a first threshold value as the given threshold value, and implements the focus control process in the second mode using a second threshold value that differs from the first threshold value as the given threshold value.

14. The focus control device as defined in claim 5, wherein the processor implements the region setting process that changes at least one of positions, a size, and a number of the regions to be set to the captured image when the focus control process has set a mode to the second mode as compared with a case where the focus control process has set the mode to the first mode.

15. A focus control device comprising:
a processor comprising hardware, the processor being configured to implement:
an region setting process that sets a plurality of regions to a captured image that has been captured by an image sensor, each of the plurality of regions including a plurality of pixels;
an object distance information calculation process that calculates distance information about a distance to an object that is captured within each of the plurality of regions; and
a focus control process based on the distance information,
wherein the processor implements the focus control process that performs a classification process that classifies the plurality of regions into a plurality of groups based on the distance information, and brings a group among the plurality of groups into focus, the group that is brought into focus having an area which has been determined to be equal to or larger than a given threshold value based on area information about each of the plurality of groups,
wherein the processor implements the object distance information calculation process that calculates reliability that represents probability that the distance information calculated with respect to each of the plurality of regions is reliable, and
wherein the processor implements the focus control process that sets a null region based on the reliability, the null region being a region that is not subjected to the classification process.

16. The focus control device as defined in claim 1, wherein the processor implements the object distance information calculation process that acquires phase difference information from a phase sensor with respect to each of the plurality of regions, and calculates the distance information based on the phase difference information.

17. The focus control device defined in claim 16, wherein the processor implements the region setting process that sets the plurality of regions based on placement information about the phase sensor in the image sensor.

18. A focus control device comprising:
a processor comprising hardware, the processor being configured to implement:
a region setting process that sets a plurality of regions to a captured image that has been captured by an image sensor, each of the plurality of regions including a plurality of pixels;
an object distance information calculation process that calculates distance information about a distance to an object that is captured within each of the plurality of regions; and
a focus control process based on the distance information,
wherein the processor implements the focus control process that performs a classification process that classifies the plurality of regions into a plurality of groups based on the distance information, and brings a group among the plurality of groups into focus, the group that is brought into focus having an area which has been determined to be equal to or larger than a given threshold value based on area information about each of the plurality of groups, and
wherein the processor implements the object distance information calculation process that calculates the distance information based on the captured image acquired by applying given patterned light.

19. An endoscope apparatus comprising the focus control device as defined in claim 1.

20. A method for controlling a focus control device comprising:
setting a plurality of regions to a captured image that has been captured by an image sensor, each of the plurality of regions including a plurality of pixels;
calculating distance information about a distance to an object that is captured within each of the plurality of regions; and
performing a classification process that classifies the plurality of regions into a plurality of groups based on the distance information, and performing a focus control process that brings a group among the plurality of groups into focus,
wherein, when it has been determined based on area information about each of the plurality of groups that an area of a largest area group, which is a group among the plurality of groups that has a largest area, is equal to or larger than a given threshold value, the processor implements the focus control process that brings the largest area group into focus.

* * * * *